(12) United States Patent
Van Erden et al.

(10) Patent No.: US 7,141,218 B2
(45) Date of Patent: *Nov. 28, 2006

(54) HIGH PRESSURE PARALLEL REACTOR WITH INDIVIDUALLY ISOLATABLE VESSELS

(75) Inventors: Lynn Van Erden, Livermore, CA (US); William H. Chandler, Jr., Milpitas, CA (US)

(73) Assignee: Symyx Technologies, Inc., Santa Clara, CA (US)

( * ) Notice: Subject to any disclaimer, the term of this patent is extended or adjusted under 35 U.S.C. 154(b) by 466 days.

This patent is subject to a terminal disclaimer.

(21) Appl. No.: 10/348,220

(22) Filed: Jan. 21, 2003

(65) Prior Publication Data

US 2003/0161763 A1   Aug. 28, 2003

Related U.S. Application Data

(63) Continuation-in-part of application No. 09/619,416, filed on Jul. 19, 2000.

(51) Int. Cl.
*B01J 19/00* (2006.01)

(52) U.S. Cl. .................................... 422/130
(58) Field of Classification Search ................ 422/130
See application file for complete search history.

(56) References Cited

U.S. PATENT DOCUMENTS

| | | | |
|---|---|---|---|
| 3,617,033 A | 11/1971 | Ichikawa et al. | 261/21 |
| 3,881,872 A | 5/1975 | Naono | 23/253 |
| 4,000,492 A | 12/1976 | Willens | 346/1 |
| 4,180,943 A | 1/1980 | Smith et al. | 49/279 |
| 4,895,706 A | 1/1990 | Root et al. | 422/102 |
| 4,990,076 A | 2/1991 | Lynch et al. | 422/112 |
| 5,011,779 A | 4/1991 | Maimon | 435/293 |
| 5,035,866 A | 7/1991 | Wannlund | 422/102 |
| 5,183,564 A | 2/1993 | Hong | 210/232 |
| 5,190,734 A | 3/1993 | Frushour | 422/242 |
| 5,205,845 A | 4/1993 | Sacks et al. | 355/197 |
| 5,246,665 A | 9/1993 | Tyranski et al. | 422/64 |
| 5,324,483 A | 6/1994 | Cody et al. | 422/101 |

(Continued)

FOREIGN PATENT DOCUMENTS

WO            97/32208            9/1997

(Continued)

OTHER PUBLICATIONS

Grunwald et al., "Investigation of Coolant Mixing in Pressurized Water Reactors at the Rossendorf Mixing Test Facility Rocom."

(Continued)

*Primary Examiner*—Yelena Gakh
*Assistant Examiner*—Natalia Levkovich
(74) *Attorney, Agent, or Firm*—Cindy Kaplan

(57) ABSTRACT

An apparatus and method for synthesis and screening of materials are disclosed. According to one aspect of the present invention, a parallel batch reactor for effecting chemical reactions includes a pressure chamber, an inlet port, and two or more reaction vessels within the pressure chamber. The inlet port is in fluid communication with the pressure chamber, and is used for pressurizing the pressure chamber from an external pressure source. Each of the two or more reaction vessels are in isolatable fluid communication with the pressure chamber such that during a first pressurizing stage of operation, each of the two or more reaction vessels can be simultaneously pressurized through common fluid communication with the pressure chamber. In addition, during at least a second reaction stage of operation, each of the two or more pressurized reaction vessels can be isolated from each other.

17 Claims, 17 Drawing Sheets

U.S. PATENT DOCUMENTS

| | | | |
|---|---|---|---|
| 5,428,118 A | 6/1995 | Painter et al. | 526/65 |
| 5,443,791 A | 8/1995 | Cathcart et al. | 422/65 |
| 5,516,490 A | 5/1996 | Sanadi | 422/101 |
| 5,529,756 A | 6/1996 | Brennan | 422/131 |
| 5,593,642 A | 1/1997 | DeWitt et al. | 422/131 |
| 5,624,815 A | 4/1997 | Grant et al. | 210/405 |
| 5,716,584 A | 2/1998 | Baker et al. | 422/131 |
| 5,746,982 A | 5/1998 | Saneii et al. | 422/134 |
| 5,766,556 A | 6/1998 | DeWitt et al. | 422/131 |
| 5,792,430 A | 8/1998 | Hamper | 422/131 |
| 5,897,842 A | 4/1999 | Dunn et al. | 422/131 |
| 5,961,925 A * | 10/1999 | Ruediger et al. | 422/99 |
| 6,027,694 A | 2/2000 | Boulton et al. | 422/102 |
| 6,042,789 A | 3/2000 | Antonenko et al. | 422/101 |
| 6,063,633 A | 5/2000 | Willson, III | 436/37 |
| 6,132,686 A * | 10/2000 | Gallup et al. | 422/130 |
| 6,149,882 A | 11/2000 | Guan et al. | 422/211 |
| 6,171,555 B1 | 1/2001 | Cargill et al. | 422/104 |
| 6,250,707 B1 | 6/2001 | Dintner et al. | 296/76 |
| 6,264,891 B1 | 7/2001 | Heynaker et al. | 422/64 |
| 6,309,608 B1 | 10/2001 | Zhou et al. | 422/131 |
| 2002/0124897 A1 | 9/2002 | Bergh et al. | 137/885 |
| 2002/0141900 A1* | 10/2002 | Guan et al. | 422/68.1 |

FOREIGN PATENT DOCUMENTS

| | | |
|---|---|---|
| WO | 97/45443 | 12/1997 |
| WO | 98/15813 | 4/1998 |
| WO | 98/36826 | 8/1998 |
| WO | 00/03805 | 1/2000 |
| WO | 00/14529 | 3/2000 |
| WO | 00/45954 | 8/2000 |
| WO | 01/00315 | 1/2001 |
| WO | 01/02089 | 1/2001 |
| WO | 01/05497 | 1/2001 |
| WO | 02/07873 | 1/2002 |

OTHER PUBLICATIONS

Heiszwolf, Johan J. "Runaway in Stirred Tanks" http://www.dct.tudelft.nl/monoliet/heiszwolf/runaway.html.

http://www.louisville.edu/speed/Mising_Lab.htm.

http://epa.gov/ORD/NRMRL/Pubs/2001/water/600r01021c2.pdf/.

Product Brochure "Calypso System Valve Base Reaction Frame"; Charybdis Technologies, Inc.

Christian Hoffmann, Anne Wolf and Ferdi Schuth, "Parallel Synthesis and Testing of Catalysts under Nearly Conventional Testing Conditions" Angew. Chem. Int. Ed 1999, 38, No. 18.

Rich et al., "An 8-Bit Microflow Controller User Pneumatically-Actuated Valves", pp. 130-134, IEEE (1999).

Wang et al., "A Parylene Micro Check Valve", pp. 177-182, IEEE (1999).

Zdeblick et al., "Thermpneumatically Actuated Microvalves and Integrated Electro-Fluidic Circuits", pp. 251-255, TRF, Solid State Sensor and Actuator Workshop, Hilton Head, South Carolina, Jun. 13-16, (1994).

Grosjean et al., "A Practical Thermpneumatic Valve", pp. 147-152, IEEE (1999).

Product Brochure for Radleys Titan Specialist Micro Titer Plates, 8 pages.

* cited by examiner

HIGH PRESSURE PARALLEL REACTOR WITH INDIVIDUALLY ISOLATABLE VESSELS

RELATED APPLICATION

This patent application is a continuation-in-part of U.S. patent application Ser. No. 09/619,416, filed Jul. 19, 2000, which is incorporated herein by reference in its entirety.

FIELD OF THE INVENTION

The present invention relates generally to parallel batch reactors, and more particularly, to high pressure parallel batch reactors for parallel synthesis and screening of materials.

BACKGROUND OF THE INVENTION

The discovery of new materials with novel chemical and physical properties often leads to the development of new and useful technologies. The discovery of new materials depends largely on the ability to synthesize and analyze new compounds. Scientists are thus, always searching for a more efficient, economical, and systematic approach for the synthesis of novel materials. Combinatorial technologies are used to accelerate the speed of research, maximize the opportunity for breakthroughs, and expand the amount of available information. Combinatorial chemistry typically involves synthesizing smaller scale quantities of thousands of an element, compound, or composition and then testing the thousands of materials quickly.

The use of combinatorial technologies allows high density libraries of very large numbers of materials to be created using parallel synthesis. High throughput screens are then used to test these materials for desired properties to identify potential optimized compounds. Combinatorial technologies may be used to optimize and validate many variations of a material, formulation, or microdevice. Variables such as temperature, pressure, atmosphere, and concentration may be quickly adjusted and tested in a single experiment.

In parallel synthesis, different compounds are synthesized in separate vessels, often in an automated fashion. A commonly used format for parallel synthesis is a multi-well microtiter plate. Robotic instrumentation may be used to add different reagents or catalysts to individual wells of a microtiter plate in a predefined manner to produce combinatorial libraries. Devices have been developed for automating combinatorial parallel synthesis. One such device includes reaction blocks containing multiple reaction vessels that are each individually sealed to prevent cross-talk between different vessels. These devices often require substantial sealing arrangements, and while successful in preventing cross-contamination, do not provide means for pressurizing the individual vessels to a desired pressure of interest, and independent of the P-T relationship inherent upon heating of the reaction vessels. Other devices supply an inert gas to a plurality of reactor vessels; however, the gas is only supplied at one or two psi above atmospheric pressure to control the environment during the reaction. These devices are not designed to withstand high pressure operation.

Therefore, what is needed is a system which is suitable for high pressure operation, and allows individual vessels to be pressurized and individually sealed.

SUMMARY OF THE INVENTION

An apparatus and method for synthesis and screening of materials are disclosed. According to one aspect of the present invention, a parallel batch reactor for effecting chemical reactions includes a pressure chamber, an inlet port, and two or more reaction vessels within the pressure chamber. The inlet port is in fluid communication with the pressure chamber, and is used for pressurizing the pressure chamber from an external pressure source. Each of the two or more reaction vessels are in isolatable fluid communication with the pressure chamber such that during a first pressurizing stage of operation, each of the two or more reaction vessels can be simultaneously pressurized through common fluid communication with the pressure chamber. In addition, during at least a second reaction stage of operation, each of the two or more pressurized reaction vessels may be isolated from each other. In one embodiment, the pressure chamber includes a pressure chamber cover and a pressure chamber base, and the two or more reaction vessels are an array of reaction vessels formed in or supported by a common substrate. In such an embodiment, the pressure chamber base is adapted for receiving the array of reaction vessels. In this embodiment, the parallel batch reactor apparatus may further comprise a cover member comprising an array of valves, such as check valves or isolation valves. Isolation valves may be actuated or controlled by a control system integral with the cover member, or integral with an actuating substrate acting in concert with the valves of the cover member.

In another embodiment, the apparatus includes an array of microvalves. For example, a pneumatically actuated microvalve array may include a plurality of microvalves in operational communication with microvalve actuators arranged on or in a common substrate. The microvalves may be integrally formed with the base or contained within a separate substrate positioned adjacent to the base.

The above is a brief description of some deficiencies in the prior art and advantages of the present invention. Other features, advantages, and embodiments of the invention will be apparent to those skilled in the art from the following description, drawings, and claims.

BRIEF DESCRIPTION OF THE DRAWINGS

The invention may best be understood by reference to the following description taken in conjunction with the accompanying drawings in which.

Corresponding reference characters indicate corresponding parts throughout the several views of the drawings.

DESCRIPTION OF SPECIFIC EMBODIMENTS

The following description is presented to enable one of ordinary skill in the art to make and use the invention. Descriptions of specific embodiments and applications are provided only as examples and various modifications will be readily apparent to those skilled in the art. The general principles described herein may be applied to other embodiments and applications without departing from the scope of the invention. Thus, the present invention is not to be limited to the embodiments shown, but is to be accorded the widest scope consistent with the principles and features described herein. For purpose of clarity, details relating to technical material that is known in the technical fields related to the invention have not been described in detail.

Figure 12A:
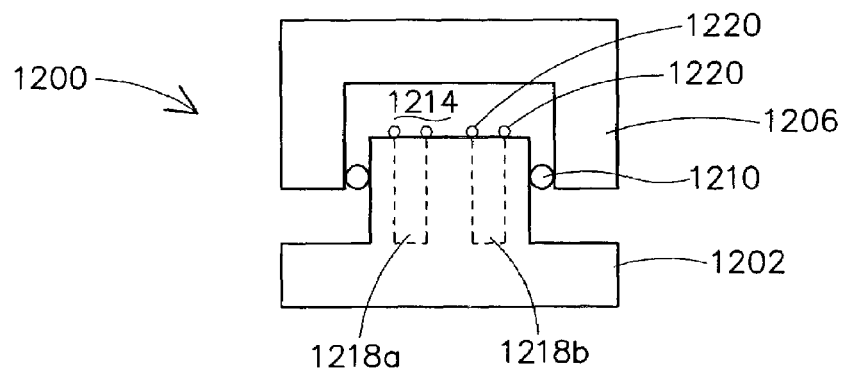
FIG. 12a is a cross-sectional representation of a pressure reactor with a seal in accordance with an embodiment of the present invention.

A system which is suitable for high pressure operation, and allows individual vessels to be pressurized and individually sealed, generally includes a base and a cover, as shown in FIG. 12a, which is a schematic cross-sectional representation of a high pressure parallel reactor in accordance with an embodiment of the present invention. A parallel batch reactor 1200 includes a parallel reactor support or base 1202 that is arranged to cooperate with a seal ring 1210, e.g., an o-ring, to seal against a parallel reactor cover 1206 to create a pressure chamber 1214. Base 1202 cooperates with ring 1210 and cover 1206 to create pressure chamber 1214 to prepressurize contents of reaction vessels 1218 to a common pressure. Base 1202 also serves as a support for reaction vessels 1218. While reaction vessels 1218 may be wells formed in base 1202, reaction vessels 1218 may also be vials which are positioned within base 1202. Further, although base 1202 serves as a support for reaction vessels 1218, in one embodiment, reaction vessels 1218 may be formed as a separate block which may then be coupled to base 1202.

Figure 12B:
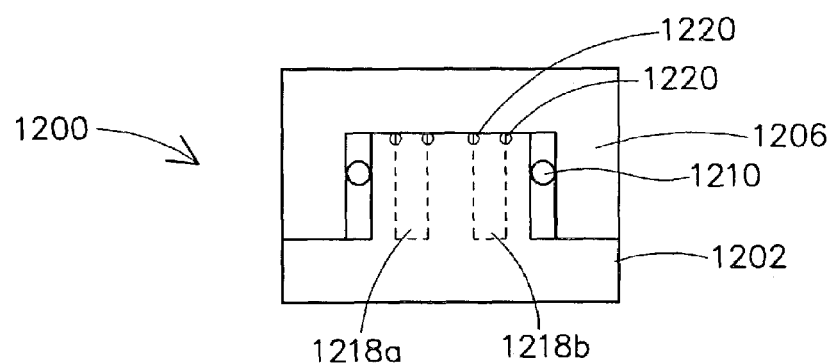
FIG. 12b is a cross-sectional representation of the pressure reactor of FIG. 12a with the seal removed in accordance with an embodiment of the present invention.

Base 1202 and cover 1206 also serve to isolate reaction vessels 1218 from one another. By way of example, base 1202, cover 1206 and seals 1220 may cooperate to fluidly isolate reaction vessel 1218a and reaction vessel 1218b from one another such that a reaction which occurs within reaction vessel 1218a substantially does not affect a reaction that occurs within reaction vessel 1218b. As shown in FIG. 12b, which is a schematic cross-sectional representation of reactor 1200, when cover 1206 is closed down against base 1202, pressure chamber 1214 effectively disappears, and reaction vessel 1218a is substantially sealed off from reaction vessel 1218b, as base 1202 and cover 1206 substantially clamp seals 1220 therebetween. It should be appreciated that seal ring 1210 may optionally be removed, e.g., when parallel batch reactor 1200 is to be exposed to relatively high temperatures.

Figure 13A:
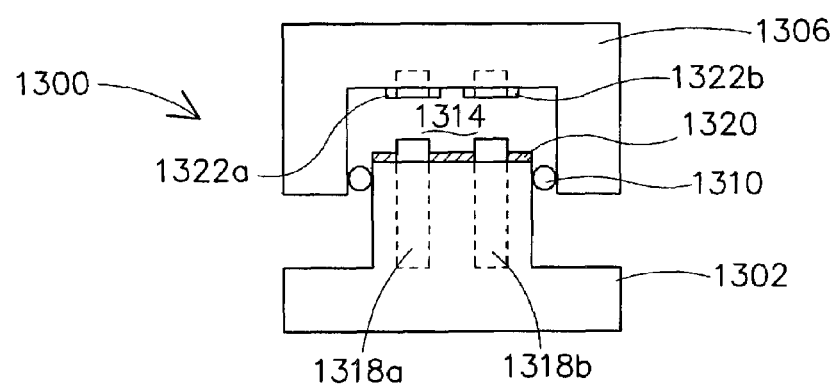
FIG. 13a is a cross-sectional representation of a pressure reactor with a first seal and a second seal in accordance with an embodiment of the present invention.

Typically, a second seal (not shown) facilitates the isolation of reaction vessel 1218a from reaction vessel 1218b. FIG. 13a is a schematic cross-sectional representation of a parallel batch reactor which uses both a first seal and a second seal in accordance with an embodiment of the present invention. A reactor 1300 includes a base 1302, a cover 1306, and a first seal 1310. Base 1302 and cover 1306 are arranged to cooperate with first seal 1310 to define a pressure chamber 1314, when base 1302 and cover 1306 are in a first orientation, or first stage of engagement, as shown. Pressure chamber 1314 enables reactor vessels 1318, which are included in base 1302 and are arranged to hold reactants, to be pressurized substantially simultaneously, as for example with a gaseous reagent. A second seal 1320 is positioned over base 1302 such that reactor vessels 1318 effectively protrude through second seal 1320.

Figure 13B:
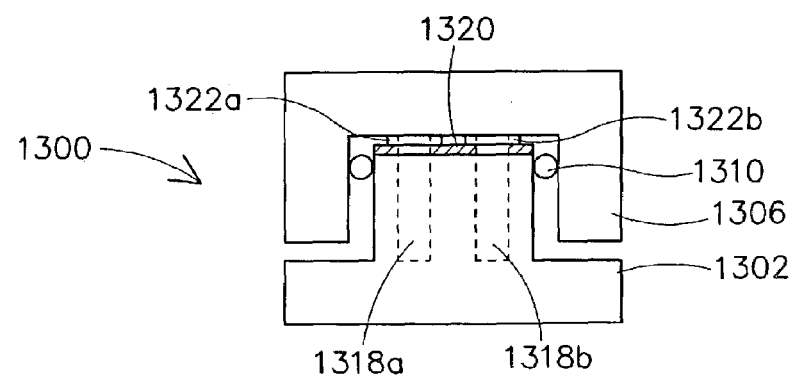
FIG. 13b is a cross-sectional representation of the pressure reactor of FIG. 13a with the first seal removed in accordance with an embodiment of the present invention.

Cover 1306 includes receptacles 1322 which are arranged to effectively engage second seal 1320 to isolate reaction vessel 1318a from reaction vessel 1318b from each other when cover 1306 and base 1302 are in a second orientation, or second stage of engagement. FIG. 13b is a schematic cross-sectional representation of parallel batch reactor 1300 in a second stage of engagement in accordance with an embodiment of the present invention. With first seal 1310 is removed, second seal 1320 may be sealed between receptacles 1322 and vase 1302, as shown, to isolate reaction vessel 1318a from reaction vessel 1318b. Hence, the amount of cross-talk between reaction vessel 1318a and 1318b may be reduced.

An apparatus which serves as both a pressure chamber and a reactor allows the pressurization of the contents of vessels in the apparatus, as well as the reactions of the contents of the vessels, to occur efficiently. In one embodiment, a cover of the apparatus serves as both a pressure chamber enclosure cover and a reactor cover, while the base of the apparatus serves as both a pressure chamber enclosure base and an array of vessels. By way of example, cover 1306 of FIG. 13a serves as a cover for pressure chamber 1314, and also serves as a reactor cover, as shown in FIG. 13b, when reactions occur within reaction vessels 1318. Similarly, base 1302 of FIG. 13*a* serves to support reaction vessels 1318, and also cooperates with cover 1306 to define pressure chamber 1314.

Alternatively, cover 1306 and base 1302 of FIG. 13*a* may each be formed as more than one piece, i.e., cover 1306 may include a pressure chamber cover component and a reactor cover component while base 1302 may include a pressure chamber base component and a reactor base component. For instance, a cover that is used as a cover for a pressure chamber, e.g., pressure chamber 1314 of FIG. 13*a*, may be substantially separate from a cover for a reactor, i.e., a cover that seals reaction vessels 1318 of FIG. 13*b*. That is, an overall cover may be formed from two substantially separate pieces. Similarly, a base that is used as a base for a pressure chamber may be substantially separate from a base that supports reaction vessels such as reaction vessels 1318 of FIG. 13*b*. In other words, a pressure chamber base may be substantially separate from a reactor base.

When a pressure chamber cover and a reactor cover are not integrally formed as a single cover such as cover 1306 of FIG. 13*a*, a seal or seals may be located between the pressure chamber cover and the reactor cover to facilitate sealing off reaction vessels 1318 of FIG. 13*a*. The seal or seals may be arranged to enable reaction vessels 1318 to be sealed by the pressure chamber cover, the reactor cover, or both the pressure chamber cover and the reactor cover.

Figure 1:
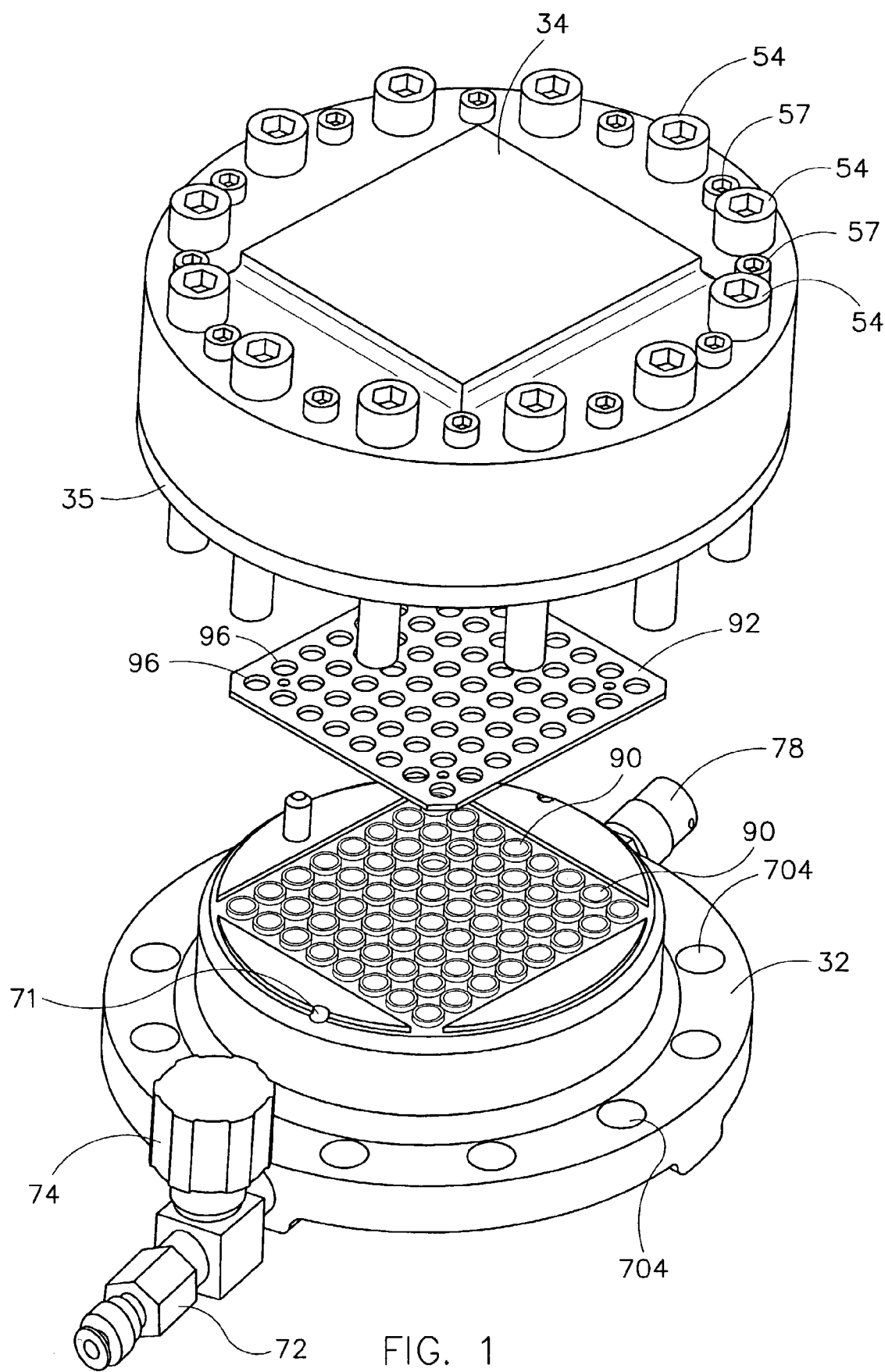
FIG. 1 is an exploded view of a reactor vessel in accordance with an embodiment of the present invention.
Figure 2:
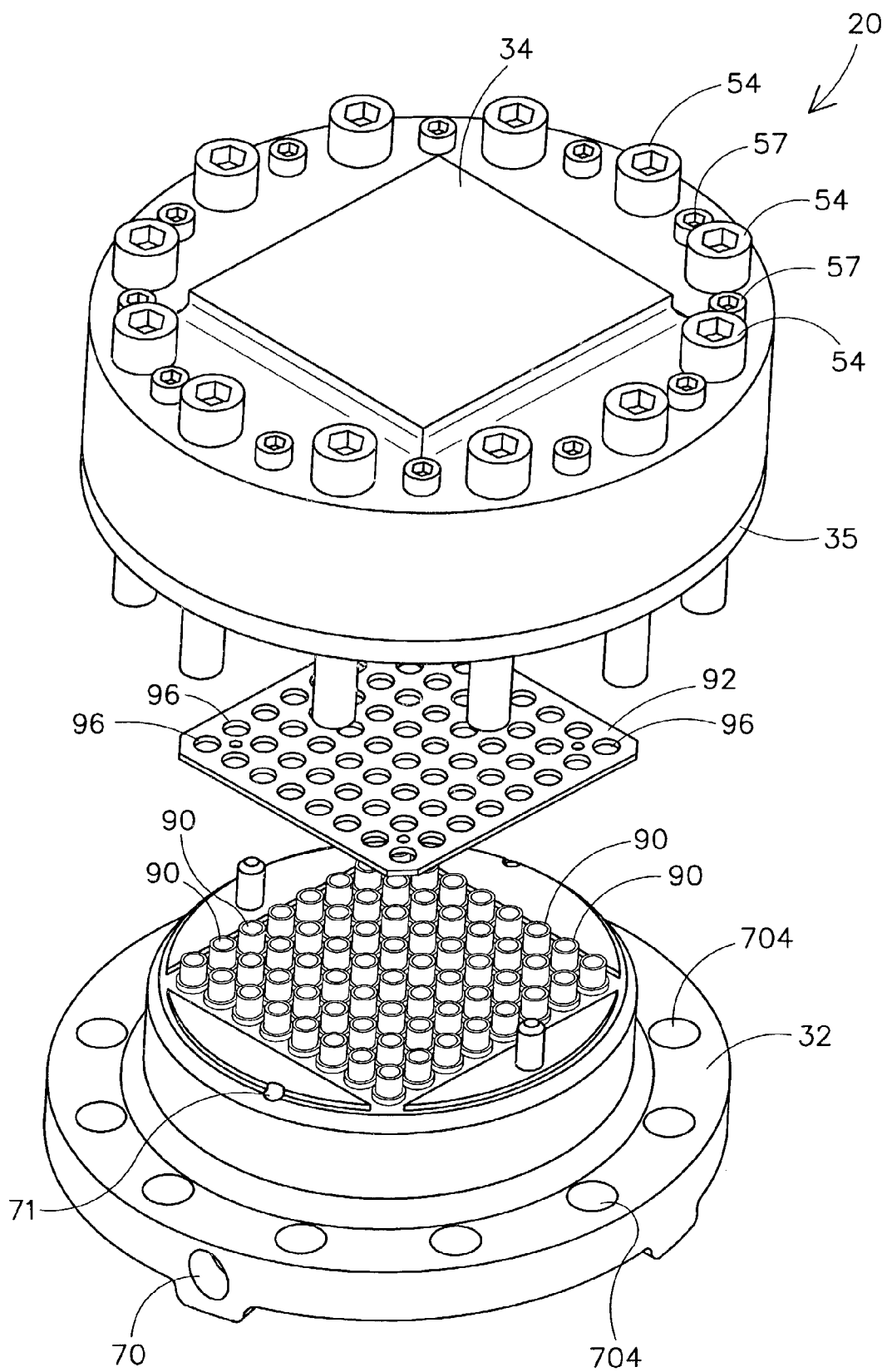
FIG. 2 is an exploded view of the reactor vessel of FIG. 1 which shows an inlet port in accordance with an embodiment of the present invention.
Figure 9A:
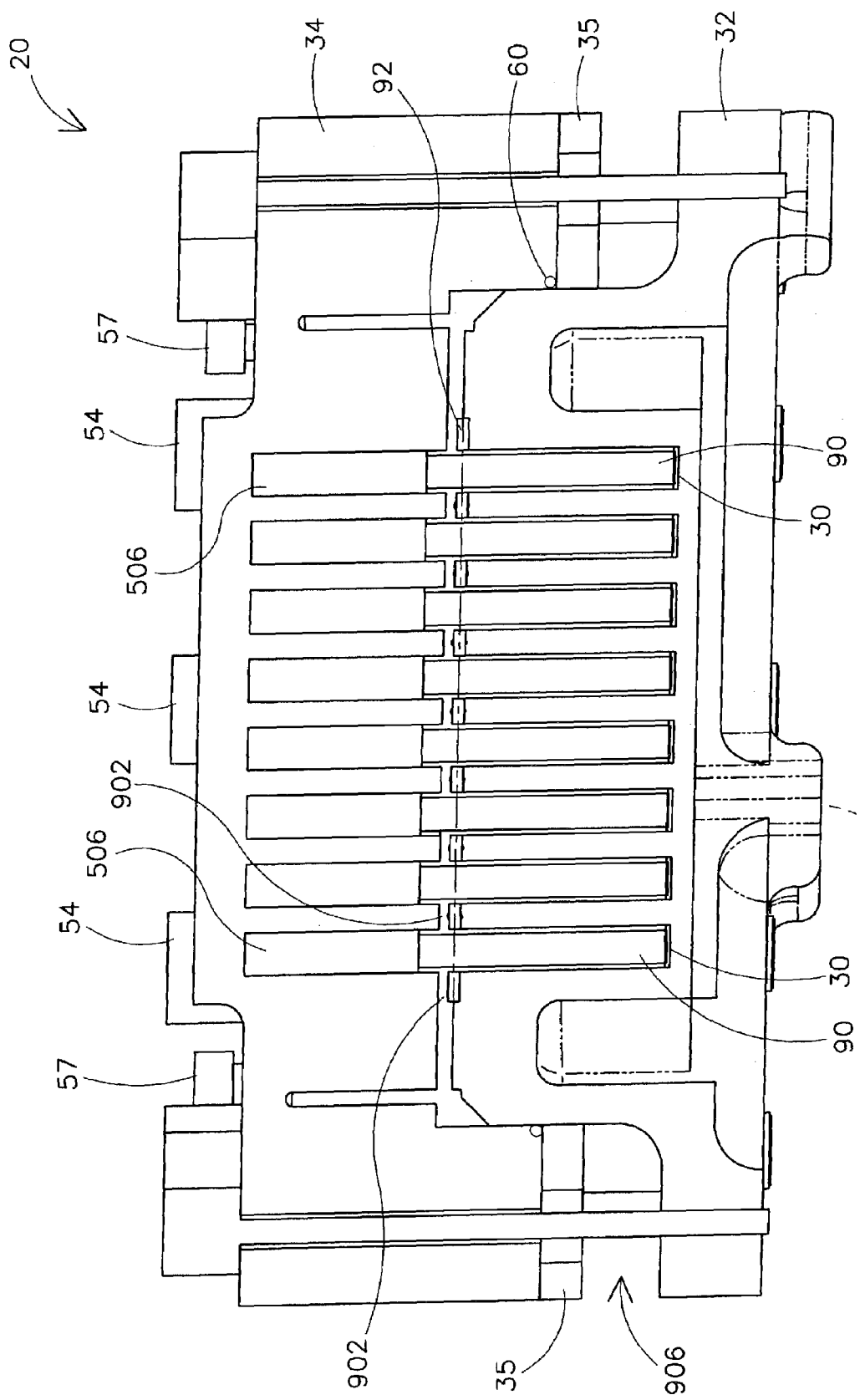
FIG. 9a is a cross-sectional view of the reactor vessel of FIG. 1 with an o-ring installed in accordance with an embodiment of the present invention.

Referring now to FIGS. 1, 2, and 9*a*, an apparatus of the present invention is shown and generally indicated at 20. Apparatus 20 comprises a reactor vessel defining a pressure chamber and a plurality of reaction wells 30 (FIG. 7) internal to the reactor vessel and exposed to the pressure chamber. Wells 30 may generally be considered to be vessels. The pressure chamber, which is defined by a gap 902, receptacles 506, and wells 30, is pressurized with an inert gas to pressurize components within the reaction wells or a gas selected to react with components within the reaction wells (FIG. 9*a*). The common pressurization area defined by the pressure chamber simplifies the sealing required as compared to individually sealed reaction wells of conventional devices. Furthermore, the common pressure chamber exposes each reaction well 30 and receptacle 506 to generally the same pressure during a pressurization process, whereas reaction wells that are individually pressurized during a pressurization process are often exposed to varying pressures due to leaks or uneven filling (when heated), which introduces undesirable variability into the testing.

Apparatus 20 may be used to perform parallel synthesis or screening of materials or other experimentation involving reactions of multiple components. For example, apparatus 20 may be utilized for reactions where one or more components is a gas such as hydrogenations, carbonilations, oxidations and polymerizations with gaseous monomers. The apparatus may also be used with homogeneous, chiral, or heterogeneous catalysts (i.e., catalysts which enable catalytic reactions to occur with the reactants and catalysts residing in different phases (e.g., solid/liquid, solid/gas, liquid/gas)), or polyolefin and butyl rubber polymerizations. It should be understood that the applications described herein are merely examples of uses of apparatus 20 and methods of the present invention and that the apparatus may be used for other applications without departing from the spirit or the scope of the invention.

Figure 4:
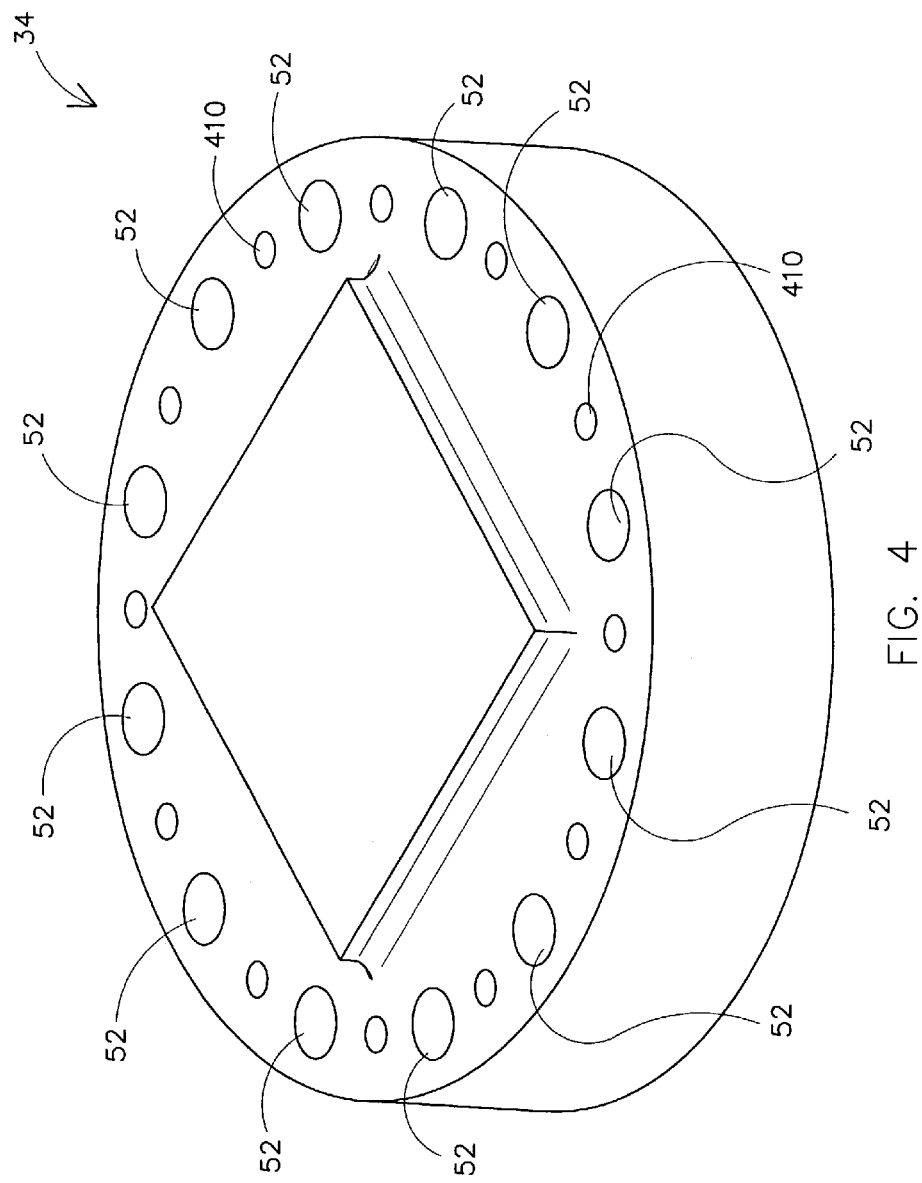
FIG. 4 is a perspective view of a topside of a cover of the reactor vessel of FIG. 1 in accordance with an embodiment of the present invention.
Figure 5:
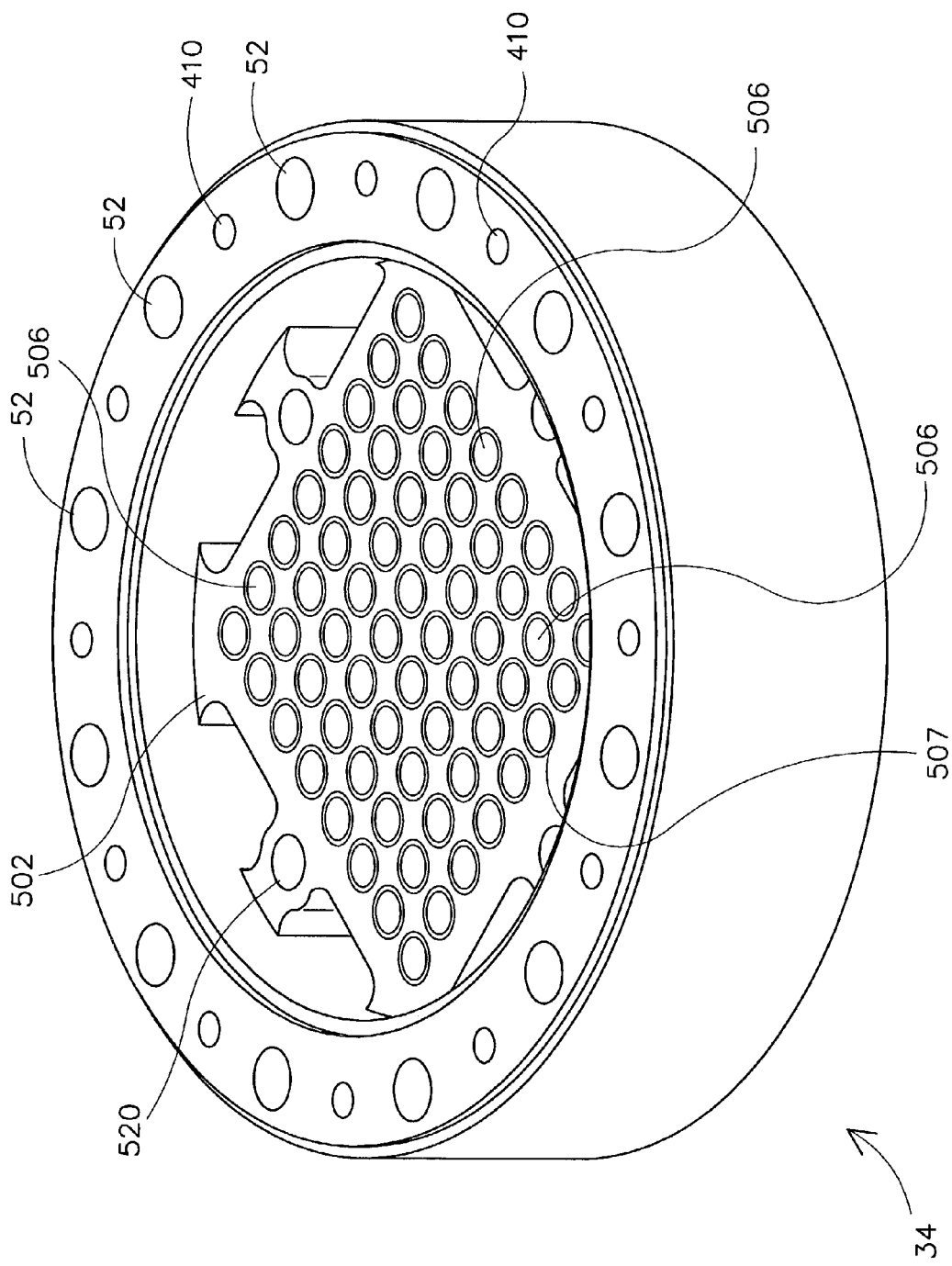
FIG. 5 is a perspective view of an underside of the cover of FIG. 4 in accordance with an embodiment of the present invention.
Figure 6:
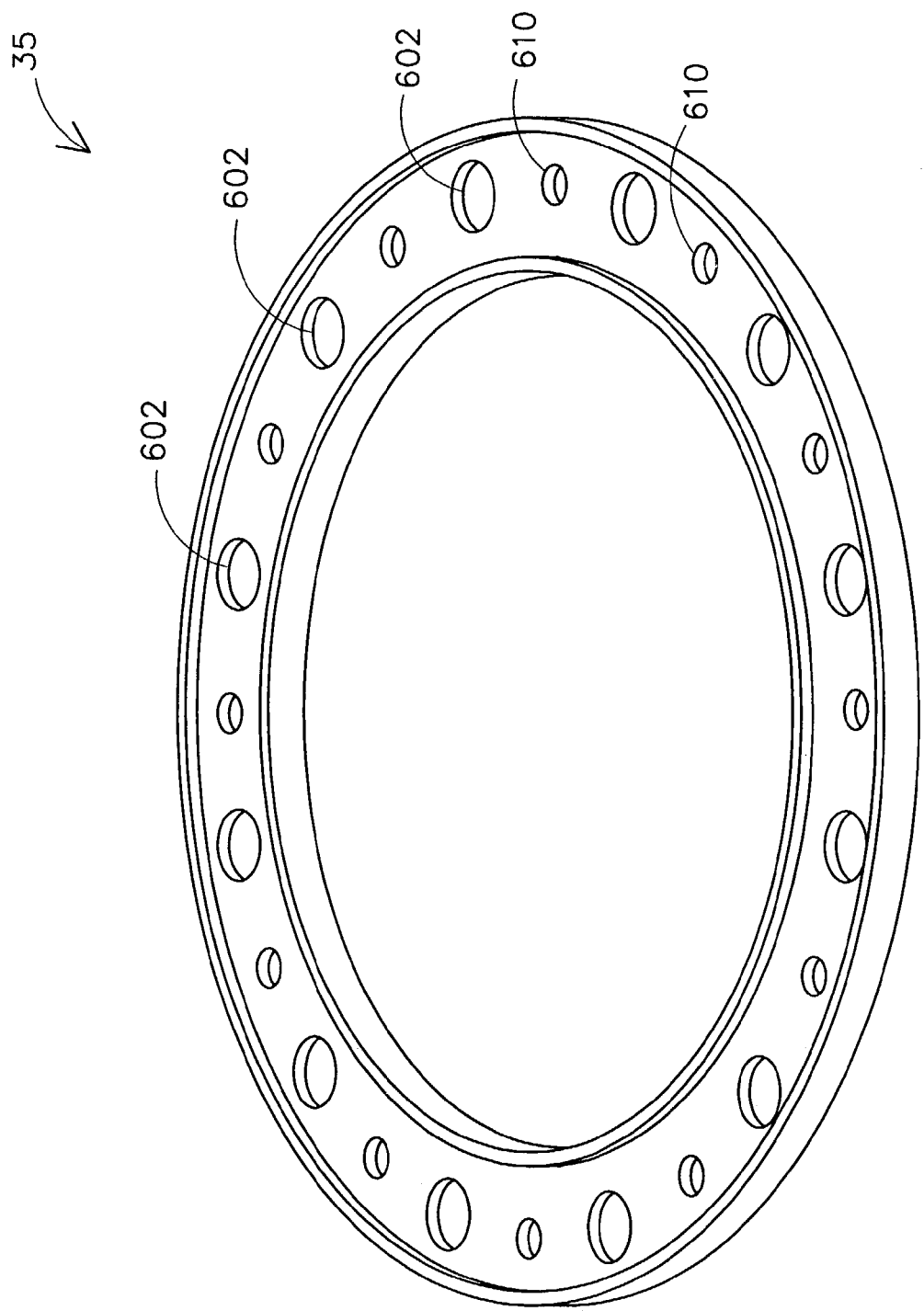
FIG. 6 is a perspective view of a ring retainer of the reactor vessel of FIG. 1 in accordance with an embodiment of the present invention.

As shown in FIGS. 1 and 2, the reactor vessel has an overall substantially circular shape and comprises two sections or members, a base member 32 and a top member (or cover) 34. It should be appreciated that reactor vessel may generally have 30 substantially any shape. The combination of base 32, i.e., a base plate, and cover 34, i.e., a part of an overall a cover assembly that may include a ring retainer 35 and an o-ring 60, form a manifold. Cover 34 is configured to mate with ring retainer 35 to secure o-ring or sealing gasket 60 (FIG. 9*a*) between cover 34, ring retainer 35, and base 32. Cover 34, as shown in FIGS. 4 and 5, includes openings 52 (twelve shown) for receiving bolts 54, screws, or other fasteners. Openings 704 (twelve shown) in base 32 (FIGS. 1, 2, 7, and 8), are aligned with openings 52 and openings 602 to receive bolts 54. Ring retainer 35, as shown in FIG. 6, also includes openings 602 (twelve shown) through which bolts 54 may pass to secure cover 34 and, hence, ring retainer 35 to base 32. Base 32, cover 34, and ring retainer 35 may also be attached by other suitable attachment means such as external clamps.

Internal surfaces of base 32 and cover 34 define an internal cavity which forms a pressure chamber defined by gap 902 (FIG. 9*a*). The volume of the pressure chamber defined by gap 902, receptacles 506, and wells 30 may vary in different embodiments. In one embodiment, the volume may be approximately five milliliters (ml), for example. Typically, the volume may be in the range of approximately one ml to approximately twenty ml.

Cover 34 and ring retainer 35 are further secured together using bolts 57 which are received in openings 410 of cover 34 and openings 610 of ring retainer 35 (FIGS. 1, 2, 4, 5, and 6). Bolts 57 may be loosened to enable sealing gasket or o-ring 60 to be removed without removing bolts 54 substantially by sliding ring retainer 35 along bolts 54, as will be described below with reference to FIG. 11. Gasket 60 is interposed between base 32, ring retainer 54, and cover 34 to essentially provide a seal between base 32 and cover 34. O-ring 60 may be formed from PTFE, neoprene, butyl rubber, Teflon coated elastomer, Viton, expanded Teflon, graphite, or Kalrez, for example. In general, o-ring 60 serves as a sliding, or dynamic, seal as o-ring 60 is typically used as a seal during a pressurization process, and is removed during a reaction process.

The reactor vessel includes an inlet port 70 in fluid communication with the pressure chamber 26, which may be substantially defined as including gap 902, receptacles 506, and wells 30. Pressure chamber 26 is similar to pressure chamber 1214, which is shown in FIG. 12*a*. A quick release fitting 72 is preferably coupled to inlet port 70 for attaching the port to a flexible hose or rigid tube (not shown) connected to a pressure supply device (FIG. 1). The flexible hose or rigid gas supply tube may also be left connected and the fill valve open during an experiment to enable gas passages, such as gas passage 71, associated with base 32, to be filled. In one embodiment, gas passage 71 and, hence, inlet port 70 may be used to enable gas to be vented. In other words, inlet port 70 may serve the purpose of an outlet port. If a vacuum is to be applied to the pressure chamber defined by gap 902, receptacles 506, and wells 30, a vacuum supply device may also be attached to pressure port 70 or another inlet port on the reactor vessel (FIGS. 1 and 9*a*).

A fill valve 74 is attached to the inlet port to control the application of pressure to the vessel (FIG. 1). Fill valve 74 may have a manual or electronic pressure control valve. A pressure sensor (not shown) may be inserted in line with fill valve 74 or inserted into the pressure chamber defined by gap 902, receptacles 506, or one or more of reaction wells 30 to monitor the pressure within the vessel (FIGS. 1 and 9*a*). The inlet supply system may allow for a series of purging, venting, or pressurization cycles, with one or more gases or with vacuum without disconnecting the supply lines. The pressure source may be an inert gas such as nitrogen, argon, or helium, or a reactive gas such as hydrogen, oxygen, hydrogen chloride, or ammonia. As will be appreciated by those skilled in the art, mixtures of gases may also be used. The reactor vessel further includes an opening for a pressure release valve 78 to prevent over pressurization of the vessel.

Base 32, cover 34, and ring retainer 35 may be formed from aluminum, titanium, steel, or any other suitable material. The material of the reactor vessel is preferably selected to be chemically inert to the reaction of interest and to allow the vessel to operate at a relatively high temperature (e.g., 150–250° C.) and a relatively high pressure (10–1500 psig). For example, if the apparatus is to be operated at 290 psig and 150° C. (for e.g., gaseous monomer or reagent use), 6061-T6 aluminum, which has been hard anodized, may be used. If the operating pressure is 1000 psig and operating temperature is 200° C., the material may be 17-4PH, H1100 stainless steel or 6A1-4V titanium. For some applications, the stainless steel or other material may be coated or surface treated. It is to be understood that the temperature or pressure applied to the reactor vessel or the materials used to form base 32 and cover 34 may be different than described herein without departing from the scope of the invention. The reactor vessel is preferably designed to withstand pressures substantially above atmospheric pressure (i.e., 14.7 psi). The vessel is preferably designed to withstand pressures above 10 psig, and more preferably pressures above 50 psig. The vessel may also be designed, for example, to operate at pressures of 15 psig, 20 psig, 30 psig, 40 psig, 100 psig, 300 psig, 500 psig, 1000 psig, 2000 psig, 3000 psig or other selected pressures. The vessel is preferably designed to withstand temperatures up to 200° C., but may also be designed to operate at 250° C., 315° C., or even higher temperatures.

Figure 7:
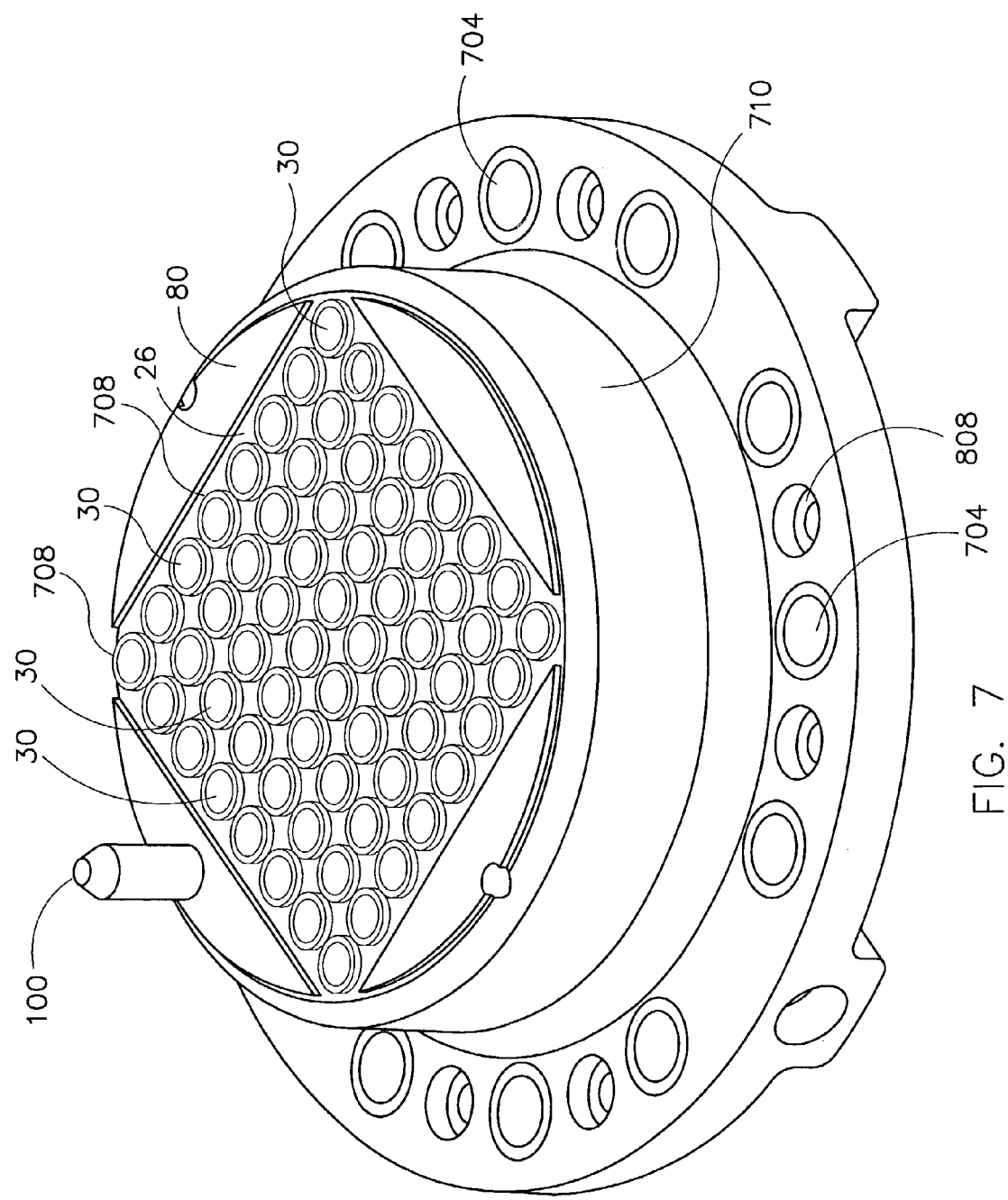
FIG. 7 is a perspective view of the topside of a base of the reactor vessel of FIG. 1 in accordance with an embodiment of the present invention.
Figure 8:
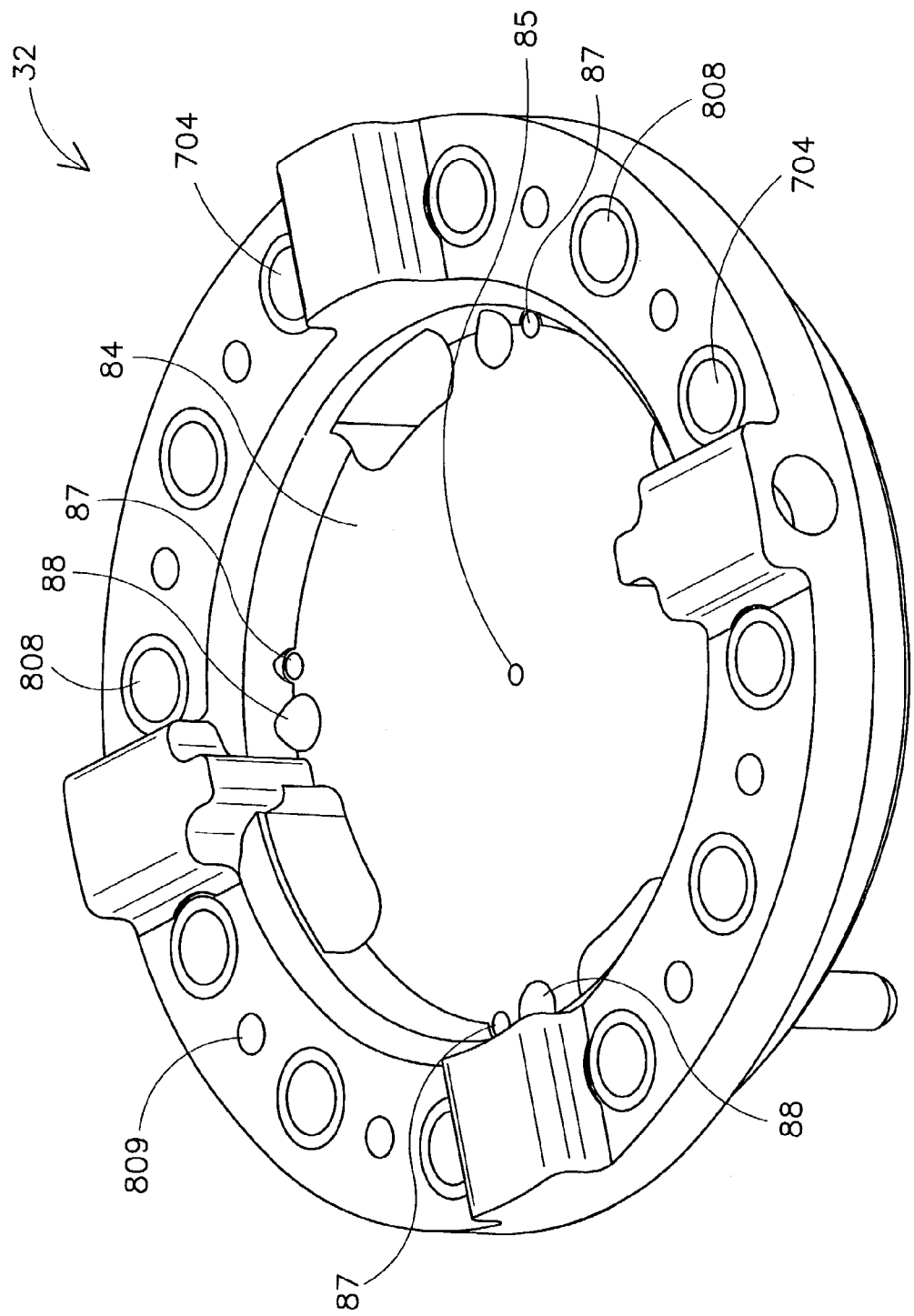
FIG. 8 is a perspective view of the underside of the base of FIG. 7 in accordance with an embodiment of the present invention.

Reaction wells 30 are preferably integrally formed within base 32 or another member coupled to base 32 (FIGS. 7 and 8). As shown in FIG. 7, wells 30 are machined into an upper planar surface 80 of base 32. Wells 30 may be machined as close as possible to one another. Alternatively, wells 30 may be machined such that wells are separated from one another for temperature control purposes, or to facilitate sealing wells 30 by providing a sealing surface between wells 30. A bottom surface (not shown) of wells 30 is left with sufficient material to withstand pressures applied to wells 30. Base 32 may also serve as a temperature control means for controlling the reaction temperature in reaction wells 30, in which case the bottom surface of reaction wells 30 is sized to provide the required conductivity between an external heat source, such as a heating plate on which the reaction vessel is placed, and reaction wells 30. The overall parallel reactor or reaction vessel may be placed, for example, on a temperature control plate which is contiguous to the lower surface of the reactor vessel for the transfer of thermal energy therebetween. The thermal control plate may be a plate formed of thermally conductive material with passages for conveying a heating or cooling fluid through the plate, or other heat generating device, as is well known by those skilled in the art. If the reactor vessel is designed for heating components within reaction wells 30, the manifold, which includes cover 34 and base 32, is preferably formed from a thermally conductive material, such as an aluminum alloy. The reactor vessel may also be placed in an oven to heat the components within reaction wells 30. As shown in FIG. 8, a bottom surface 84 may be configured to attach to devices associated with the heating or the cooling of materials in reaction wells 30. For example, an opening 85 may be configured to effectively attach a thermocouple or similar device to bottom surface 84, and openings 87 may be configured to facilitate the installation of a heater. Specifically, openings 87 may be used to secure a heater to an openings 88. Openings 808, which are generally counter-bored (as shown in FIG. 7), enable base 32 to be installed on a device such as an orbital shaker.

Cover 34 is configured such that a base interface side 502 of cover 34 includes receptacles 506, as shown in FIG. 5, that are arranged to line up with reaction wells 30. That is, receptacles 506 are arranged to essentially line up with reaction wells 30 such that when cover 34 is secured against base 32, each receptacle 506 substantially lines up to be in fluid communication with each reaction well 30. In one embodiment, when cover 34 and base 32 are positioned such that a locating pin 100 of base 32 (FIGS. 1, 2, and 7) is positioned within a locating opening 520 of cover 34 (FIG. 5), reaction wells 30 and receptacles 506 are oriented such that receptacles 506 overlap wells 30.

Although reaction wells 30 are described as being formed within base 32 of the reactor vessel, reaction wells 30 may, in one embodiment, be formed within a reaction vessel block or a substrate that is separate from base 32. For example, reaction wells 32 may be formed within a metal, nylon, Teflon, or other polymer material block that may be inserted within or held within base 32. Such a reaction vessel block may be a microtiter plate, as described below.

The reaction vessel wells are preferably configured to correspond to a standard microtiter plate spacing. A microtiter plate format is a widely used means for handling, processing, and analyzing large numbers of small samples in the biochemistry and biotechnology fields. In the described embodiment, the reaction vessel wells in the microtiter plate spacing contains 64 identical sample wells in an 8 by 8 substantially square array on 4.5 millimeter or 9 millimeter centers, for example. A wide variety of equipment is available for automatic handling, processing, and analyzing of samples in this microtiter plate format for the reaction vessel wells. It is to be understood that depending upon the scale of the apparatus, the block may contain a greater or fewer number of reaction wells of various geometries arranged in any configuration.

In the embodiment shown in FIGS. 1–8, base 32 includes 64 reaction wells 30 in an 8 by 8 array, corresponding to one standard microtiter plate spacing. Reaction wells 30 may be substantially integrally supported by pressure chamber base 32. In preferred embodiments, the number of test wells is equal to 96×N, where N is an integer ranging from 1–100, preferably 1–10, and more preferably 1–5. It should be appreciated that the number of test wells may also be equal to 8×N, 16×N, 48×N, 64×N, or substantially any multiple of 96×N. The outside dimensions of the vessel preferably enable the reaction or test wells to correspond to the standard microtiter format (e.g., approximately 3.0 inches in diameter, and 2.25 inches high). It is to be understood that the reactor vessel may have a different number or arrangement of reaction wells 30 without departing from the scope of the invention. For example, the reactor may have a 3 by 4 array of reaction wells, each well having a fluid volume of approximately 16 milliliters. Other arrays, such as a 3 by 5 array or a 100 by 100 array may also be used.

Components used in the synthesis or screening may be added directly to reaction wells 30, reaction wells 30 may be lined with an inert liner to prevent reactions between chemicals and base 32. As shown in FIGS. 1 and 2, vials 90 may be inserted into wells 30 for receiving the components. Vials 90 may be formed from glass or other suitable materials, and preferably extend above the reaction well openings formed in base member 32. Glass vials 90 may have an internal volume of approximately 2 milliliters, for example, although the internal volumes may vary widely. In general, it should be appreciated that wells 30 and vials 90 that are supported in wells 30, or substantially any other suitable type of vessel, may be used to receive components or reactants.

A gasket 92 is preferably positioned with respect to reaction wells 30 to enable vials 90 to be sealed individually or in small groups when desired (FIG. 1). Gasket 92 may be aligned such that vials 90 fit through openings 96 defined within gasket 92. In one embodiment, openings 96 may be sized to enable vials 90 to fit snugly in opening such that gasket 92 may serve as a carrier to move vials 90 as an array from base 32 to another location, e.g., to a different station or a different base. That is, gasket 92 may function to clamp vials 90 in a common array.

Figure 3:
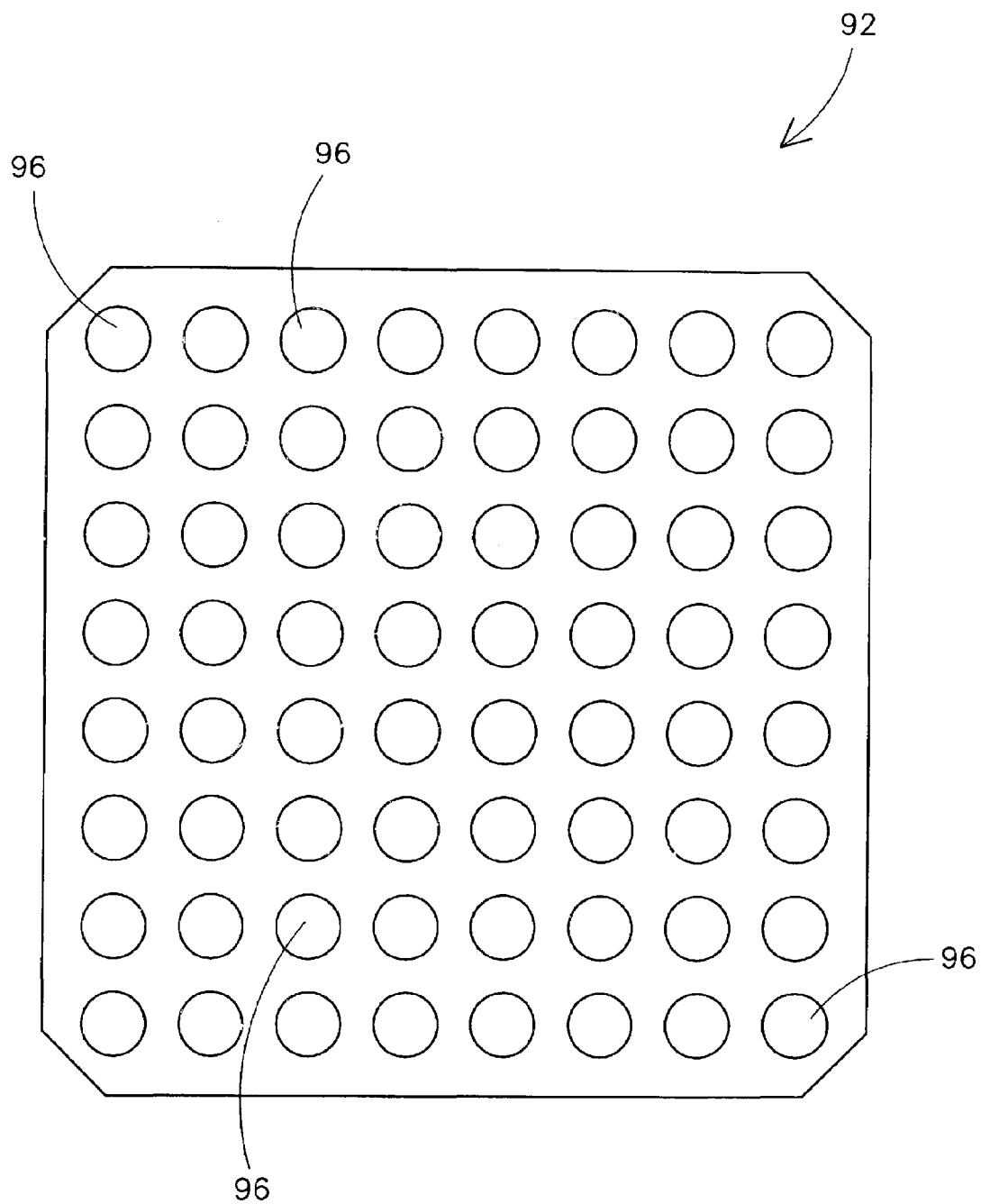
FIG. 3 is a plan view of a gasket of the reactor vessel of FIG. 1 in accordance with an embodiment of the present invention.

As shown in FIGS. 1–3, gasket 92 includes 64 openings to accommodate an array of 64 vials 90. Although substantially any suitable material may be used to form gasket 92, the gasket is typically formed from a material which promotes the individually sealing of vials 90, and is capable of withstanding relatively high temperatures, e.g., temperatures of up to 300° C. or up to 500° C. Suitable materials from which gasket 92 may be formed include, but are not limited to, Gortex and graphite.

The materials of base 32, cover 34, gasket 92, o-ring 60, and vials 90 are preferably selected to be chemically suitable for the application (i.e., will not be attacked, solubilized, softened, or otherwise interact with the reagents, solvents, solids, products, or other components which are either added to the vessel or produced during a reaction sequence). The materials are also preferably chosen to assure that reactant, products, or by-products of the reaction are not adsorbed or otherwise trapped by the materials.

FIG. 9a is a representation of apparatus 20 of FIGS. 1 and 2 in a closed configuration when o-ring 60 is used to create a gap 902 between gasket 92 and cover 34 in accordance with an embodiment of the present invention. When in a closed configuration, apparatus 20 is configured such that o-ring 60 is positioned substantially between cover 34 and ring retainer 35. The positioning of o-ring 60 enables gap 902 to exist between cover 34 and gasket 92, as shown in more detail in FIG. 10, which is a representation of apparatus 20 in a closed position. Gap 902 allows gas to flow through a passageways 910, 71, which are in fluid communication with inlet port 70 (FIG. 2), and into receptacles 506 and wells 30 in order to provide a common pressure to vials 90. Providing the common pressure to vials 90 allows a pressurizing stage of operation to occur with respect to apparatus 20. Specifically, gap 902 cooperates with receptacles 506 to provide a common headspace over vials 90 (FIG. 5).

Figure 10:
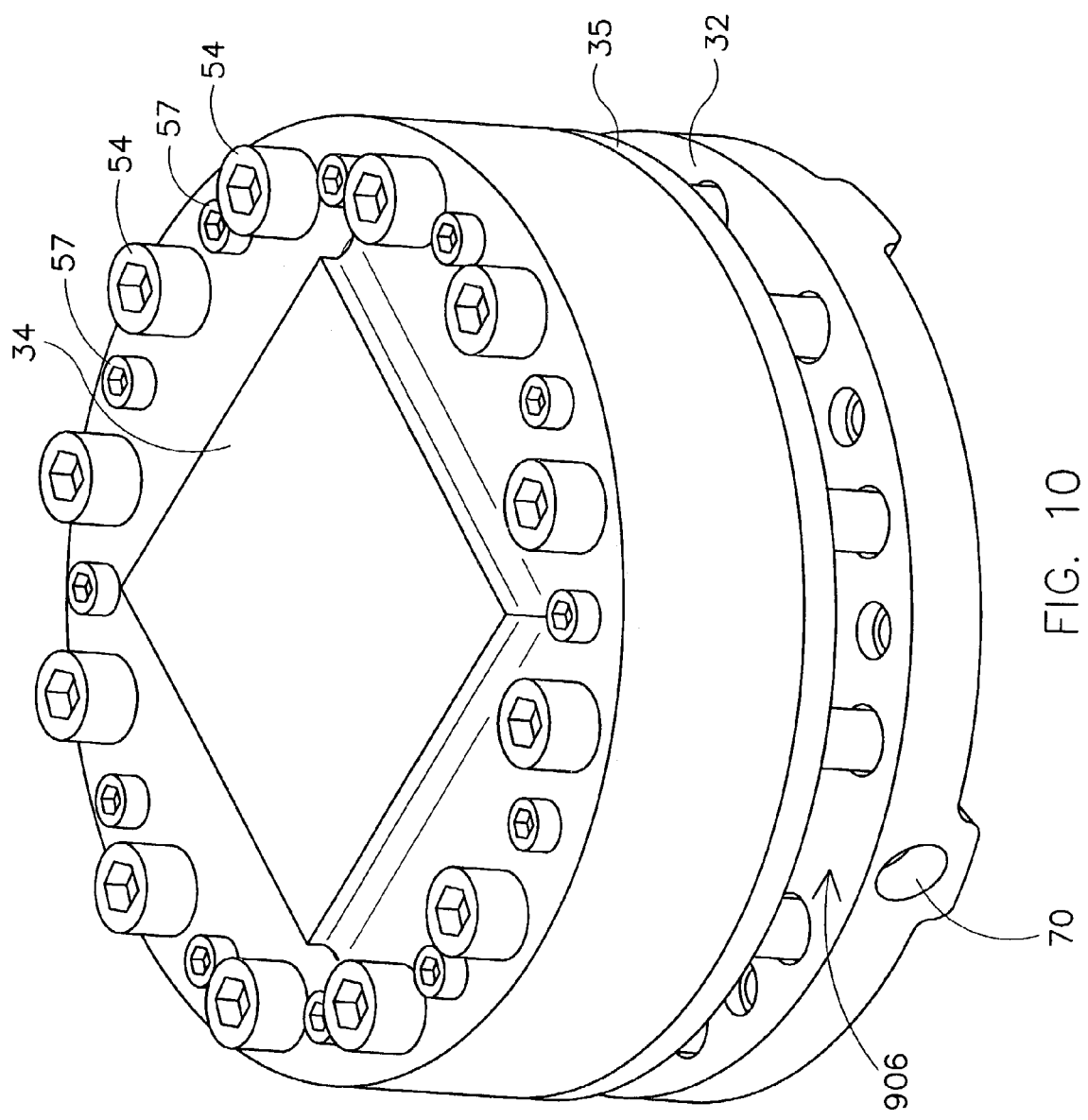
FIG. 10 is perspective representation of the reactor vessel of FIG. 1 in an assembled configuration in accordance with an embodiment of the present invention.

When apparatus 20 is in a closed position, i.e., when bolts 54 secure cover 34, and ring retainer 35 to base 32, a gap 906 is present between ring retainer 35 and base 32 (FIG. 10). The presence of gap 906 enables ring retainer 35 to effectively slide on bolts 54 between cover 34 and base 32 when bolts 57 are removed. That is, gap 906 allows the ring retainer 35 to move with respect to cover 34 when bolts 57 are removed such that o-ring 60 effectively forms a dynamic seal. Enabling ring retainer 35 to slide on bolts 54 facilitates the removal of o-ring 60 when vials 90 are to be individually sealed.

Figure 9B:
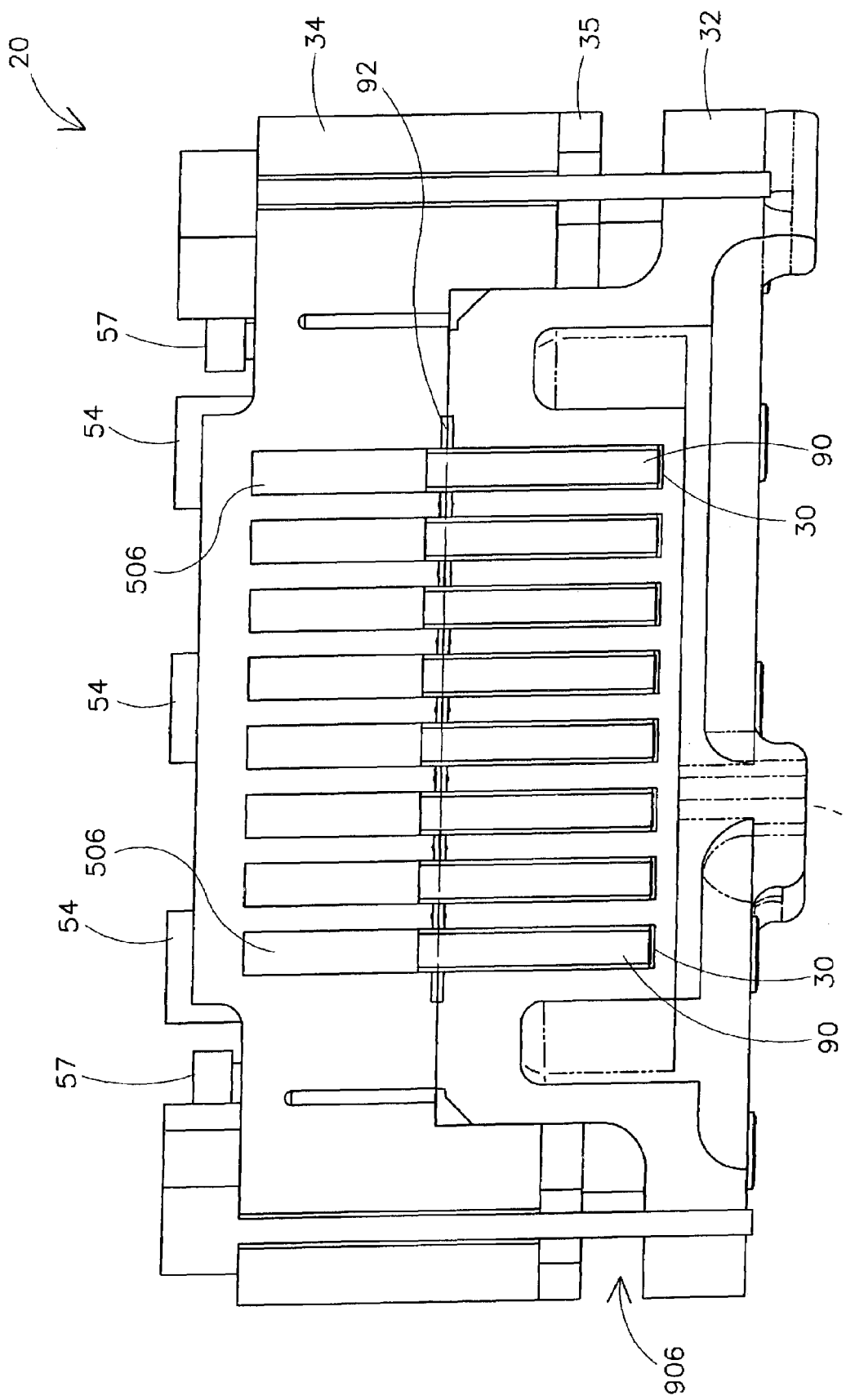
FIG. 9b is a cross-sectional view of the reactor vessel of FIG. 1 without the o-ring installed in accordance with an embodiment of the present invention.

FIG. 9b is a representation of apparatus 20 when vials 90 are individually sealed in accordance with an embodiment of the present invention. As illustrated, once gap 902 is effectively eliminated, o-ring 60 is removed from between cover 34 and ring retainer 35, and cover 34 comes into contact with gasket 92. In other words, once gap 902 is effectively eliminated, then o-ring 60 may be removed, as for example in an embodiment in which apparatus 20 is to be exposed to temperatures of above approximately 200° C. Typically, o-ring 60 may be removed from apparatus 20 by cutting the o-ring. The contact between cover 34 and both gasket 92 and base 32 creates seals substantially around each vial 90. Vials 90 or wells 30 may be individually sealed when machined or raised ridges 507 come into contact with gasket 92. In addition, machined or raised ridges 35 may come into contact with sides of receptacles 506 to further create seals around vials 90. Individually sealing each vial 90 enables reactions to occur within each vial 90 substantially without cross-contamination from other vials 90. When vials 90 are individually sealed, the operation of apparatus 20 is effectively in a reaction stage.

Figure 11:
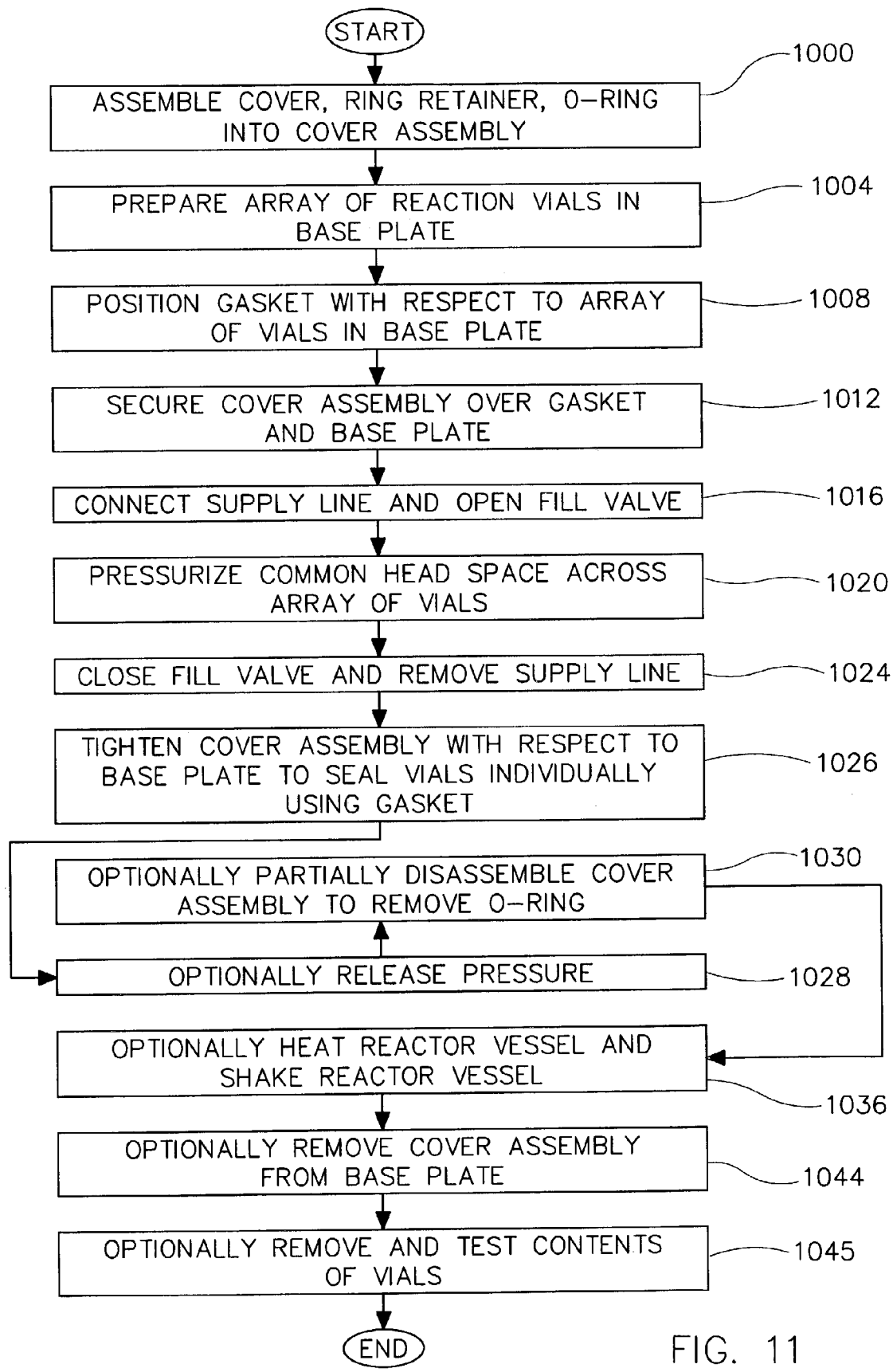
FIG. 11 is a flowchart illustrating a process utilizing the reactor vessel of FIG. 1 in accordance with an embodiment of the present invention.

FIG. 11 is a flowchart illustrating a process for utilizing apparatus 20 of the present invention. At step 1000, cover 34, ring retainer 35, and o-ring 60 are assembled together to form a cover assembly. After the cover assembly is assembled, an array of reaction vials 90 is prepared in step 1004. In one embodiment, preparing the array of reaction vials 90 may include positioning vials within wells 30 in base 32 and placing compositions of materials that are to be tested into each of vials. It should be appreciated that if the reaction wells are not formed in the base member, the block or substrate containing the reaction wells is positioned within base 32. In addition, when reaction vials 90 are not used, compositions of materials that are to be tested may be placed into wells 30. Preferably, the composition of the materials placed within each of wells 30, or reaction vials 90, varies from one reaction well to the next.

Once the array of vials 90 is prepared, gasket 92 is positioned in step 1008 with respect to the array of vials in base 32. That is, gasket 92 is positioned such that vials 90 are effectively inserted through openings 96 in the gasket. Cover 34 or cover assembly is then placed over base 32 with fastener openings 52 through which fasteners 54 may be positioned within the cover assembly aligned with openings 704 formed in the base (or reaction well block) such that the cover assembly may be secured with respect to the base in step 1012. Specifically, the cover assembly is fastened to base 32 such that the array of vials 90 may be sealed through the use of o-ring 60. That is, o-ring 60 essentially seals the cover assembly against base 32 with while maintaining a common head space over the vials, i.e., a pressure chamber is maintained between the cover assembly and the base. The common head space is possible because of gap 902 between cover 34 and gasket 92, as shown in FIG. 9a. Fastening or securing the cover assembly to base 32 may be accomplished when bolts 54, or other suitable fasteners, are inserted into the aligned openings 52, 704 to attach the cover assembly to base 32.

A supply line (not shown) is connected to quick release coupling 72 at inlet port 70 and fill valve 74 is opened in step 1016 until the required pressure is reached within the pressure chamber defined by gap 902 in step 1024 (FIGS. 1 and 2). In other words, fill valve 74 is opened until the common head space across the array of vials 90 is pressurized during a pressurization stage of operation. The gas supplied to the vessel through the supply line may be an inert gas or a gas that reacts with the components placed into vials 90.

After the pressurized gas is added to the vessel and the pressure chamber defined by gap 902 has reached the appropriate operating pressure, the fill valve 74 is closed, the supply line is removed in step 1024. Once the supply line is removed, the cover assembly is tightened with respect to gasket 92 and base 32 in order to seal vials 90 individually in step 1026. In other words, interior side 502 of cover 34 (FIG. 5) is tightened against gasket 92 such that the interior side is sealed against the gasket to effectively initiate a reaction stage of operation. In the embodiment shown in FIG. 5, interior side 502 is configured to cause each vial 90 to effectively be individually sealed using gasket 92, i.e., the interior side includes raised areas 507. It should be appreciated, however, that in some embodiments, interior side 502 may be configured to cause more sets of vials 90 to be sealed together using gasket 92. In other words, raised areas 507 may be arranged to seal together different groups of vials 90.

Pressure is optionally released from apparatus 20 in step 1028, e.g., through fill valve 74 or an outlet or vent within the apparatus. The cover assembly may then be optionally partially disassembled to remove o-ring 60 in step 10230. In one embodiment, removing o-ring 60 includes removing bolts 57 (FIGS. 1 and 2) to enable ring retainer 35 to move with respect to cover 34, and cutting the o-ring. When ring retainer 35 may move, or slide, with respect to cover 34, o-ring 60 may be removed. It should be appreciated that although o-ring 60 may remain in the cover assembly in some embodiments, when the vessel is to be exposed to relatively high temperatures, e.g., temperatures of up to approximately 300° C. or up to approximately 500° C., the o-ring is typically removed.

Upon removing o-ring 60 in step 1030, apparatus 20 may then optionally be inserted into an oven or placed on a heating plate and heated, as well as agitated, in step 1036. Agitating the components within vials 90 may be achieved by shaking or magnetic stirring. For example, apparatus 20 may be placed on an oven/shaker assembly or a magnetic stirrer may be used to mix the reactants during the reaction stage of operation. Base 32, cover 34, and ring retainer 35 are preferably aluminum or titanium if magnetic stirring is used. Once the reaction is complete, the cover assembly is optionally disengaged from base 32 in step 1044. Finally, in step 1048, the array of vials 90 is optionally removed from base 32 or, more specifically, from reaction wells 30 for analysis. Removing the array of vials 90 may be accomplished by removing gasket 92 which serves as a carrier for vials 90. For an embodiment in which vials 90 are not used, and testing components are placed directly into reaction wells 30, a pipette or other suitable tool may be used to remove contents of the wells. The contents of vials 90 or reaction wells 30 are generally analyzed by techniques well known by those skilled in the art.

As can be observed from the foregoing, apparatus 20 and method of the present invention have numerous advantages. Vials 90, or reaction wells 30 if vials 90 are not used, are all exposed to a common pressure chamber defined by gap 902 which results in simplification of the apparatus, reduced variation between pressurization of the reaction wells, and reduced manufacturing and processing costs. The apparatus is well suited for auxiliary processes including heating, shaking, and robotic automation. The design of the reactor vessel allows for pressurization of the reaction wells with a pressurized gas at a pressure substantially above atmospheric pressure.

Figure 14:
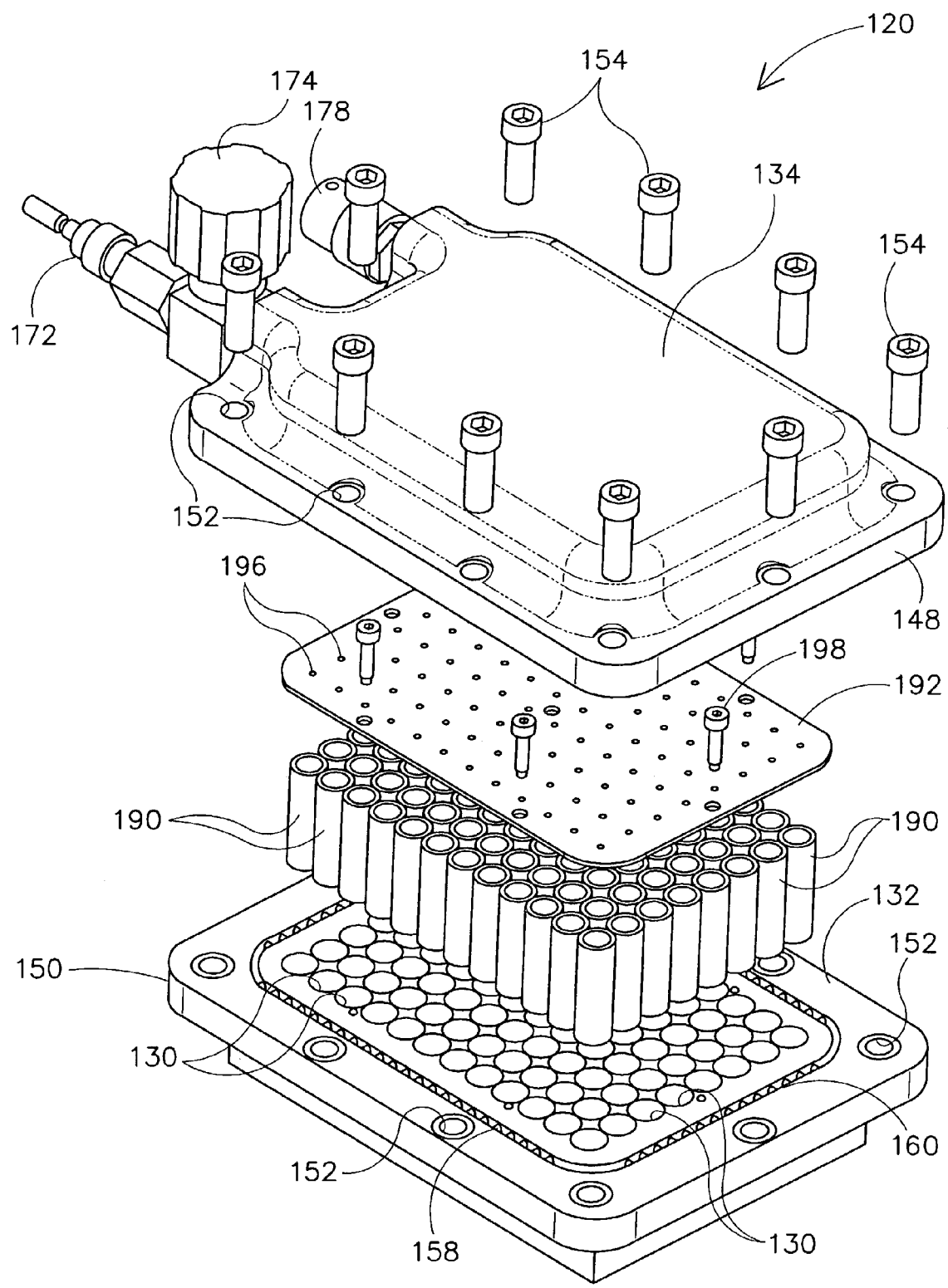
FIG. 14 is an exploded view of a second reactor vessel of the present invention that includes a flow restriction device.

In one embodiment, a flow restriction device may be placed over reaction wells or vials to reduce vapor phase cross-talk between adjacent wells. FIG. 14 is an exploded view of a second reactor vessel of the present invention that includes a flow restriction device. A reactor vessel 120 includes a base member 132 and a top member (or cover) 134. The combination of the base 132 and cover 134 form a manifold generally in the form of a rectangular parallelepiped, although the shape of the manifold may be widely varied. Internal surfaces of the base 132 and cover 134 define an internal cavity which forms the pressure chamber. The pressure chamber may have a volume of approximately ten cubic inches, for example. The cover 134 includes a periphery flange 148 configured to mate with a periphery flange 150 of the base member 132. The flanges 148, 150 of the cover 134 and base 132 include a plurality of openings 152 (ten shown) for receiving bolts 154, screws, or other fasteners. The base 132 and cover 134 may also be attached by other suitable attachment means such as external clamps. The base 132 includes a groove 158 extending around a periphery thereof for receiving a sealing gasket 160. The gasket 160 is interposed between the base 132 and cover 134 to provide a seal therebetween. The groove 158 for the gasket 160 may be machined into either a bottom surface of flange 148 of the cover 134, or a top surface of flange 150 of the base 132. The gasket 160 may be an o-ring formed from PTFE, neoprene, butyl rubber, Teflon coated elastomer, Viton, expanded Teflon, graphite, or Kalrez, for example.

A quick release fitting 172 is preferably coupled to an inlet port (not shown) for attaching the port to a flexible hose or rigid tube (not shown) connected to a pressure supply device. The flexible hose or rigid gas supply tube may also be left connected and the fill valve open during an experiment. If a vacuum is to be applied to the pressure chamber defined by the reactor vessel, a vacuum supply device may also be attached to the pressure port 170 or another inlet port on the reactor vessel. A fill valve 174 is attached to the inlet port to control the application of pressure to the vessel. The fill valve 174 may have a manual or electronic pressure control valve. A pressure sensor (not shown) may be inserted inline with the fill valve 174 or inserted into the pressure chamber or one or more of the reaction wells 130 to monitor the pressure within the vessel. The inlet supply system may allow for a series of purging, venting, or pressurization cycles, with one or more gases or with vacuum without disconnecting the supply lines. The pressure source may be an inert gas such as nitrogen, argon, helium, carbon dioxide, or air, or a reactive gas such as hydrogen, oxygen, hydrogen choride, or ammonia. Mixtures of gases may also be used. The reactor vessel further includes an opening for a pressure release valve 178 to prevent over pressurization of the vessel.

The base 132 and cover 134 may be formed from aluminum, titanium, steel, or any other suitable material. The material of the reactor vessel is preferably selected to be chemically inert to the reaction of interest and allow the vessel to operate at high temperature (e.g., 150–250° C.) and high pressure (10–1000 psig). For example, if the apparatus is to be operated at 290 psig and 150° C. (for e.g., gaseous monomer or reagent use), 6061-T6 aluminum, which has been hard anodized, may be used. If the operating pressure is 1000 psig and operating temperature is 200° C., the material may be 17-4PH, H1100 stainless steel or 6A1-4V titanium. For some applications, the stainless steel or other material may be coated or surface treated. It is to be understood that the temperature or pressure applied to the reactor vessel or the materials used to form the base 32 and cover 34 may be different than described herein without departing from the scope of the invention. The reactor vessel is preferably designed to withstand pressures substantially above atmospheric pressure (i.e., 14.7 psi). The vessel is preferably designed to withstand pressures above 10 psig, and more preferably pressures above 50 psig. The vessel may also be designed, for example, to operate at pressures of 15 psig, 20 psig, 30 psig, 40 psig, 100 psig, 300 psig, 500 psig, 1000 psig, or other selected pressures. The vessel is preferably designed to withstand temperatures up to 200° C., but may also be designed to operate at 250° C., 315° C., or higher temperatures.

Figure 15:
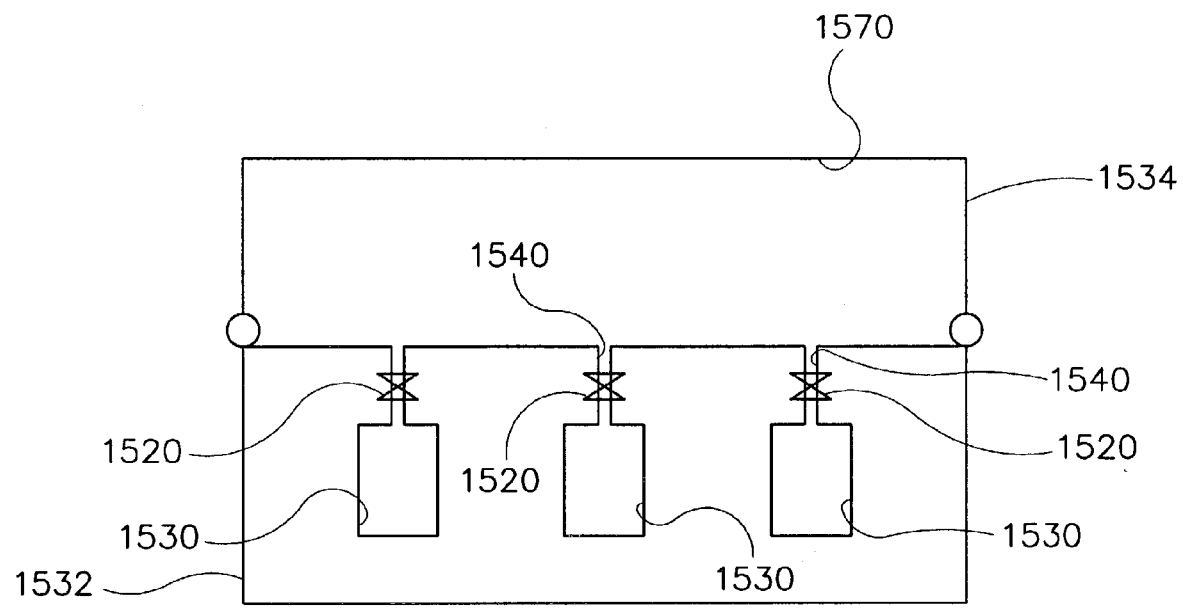
FIG. 15 is a schematic illustrating an array of microvalves integrally formed in the base of a reactor vessel.

A flow restriction device 192 may comprise, for example, a cover member having a plurality of very small vent holes 196 aligned with reaction wells 130 to provide fluid communication between the wells and the pressure chamber. Cover member 192 may be a rigid metal plate with vent holes drilled therein or a flexible elastomeric sheet (e.g., septum sheet) with vent holes punched therein. The member 192 may also be a porous sheet with the pores providing fluid communication between the reaction wells 130 and the pressure chamber. The vent holes within the flow restriction device 192 may also be micromachined flow restrictions. The flow restriction device 192 may also include check valves which allow flow into the reaction wells 130 but restrict flow from the reaction wells to the pressure chamber. In lieu of including check valves, flow restriction device 192 may also include substantially any other type of suitable valve including, but not limited to, controlled microvalves, actuated valves, and isolation valves FIG. 15 is a schematic illustrating a restriction device comprising an array of microvalves 1520 integrally formed in base 1532. The valves 1520 are preferably positioned adjacent reaction wells 1530 to restrict flow between the wells. For example, the reaction wells 1530 may be formed in the base 1532 with passageways 1540 in fluid communication with a common pressure chamber 1570 formed by cover 1534. The microvalves 1520 are positioned to restrict flow through passageways 1540.

Figure 16:
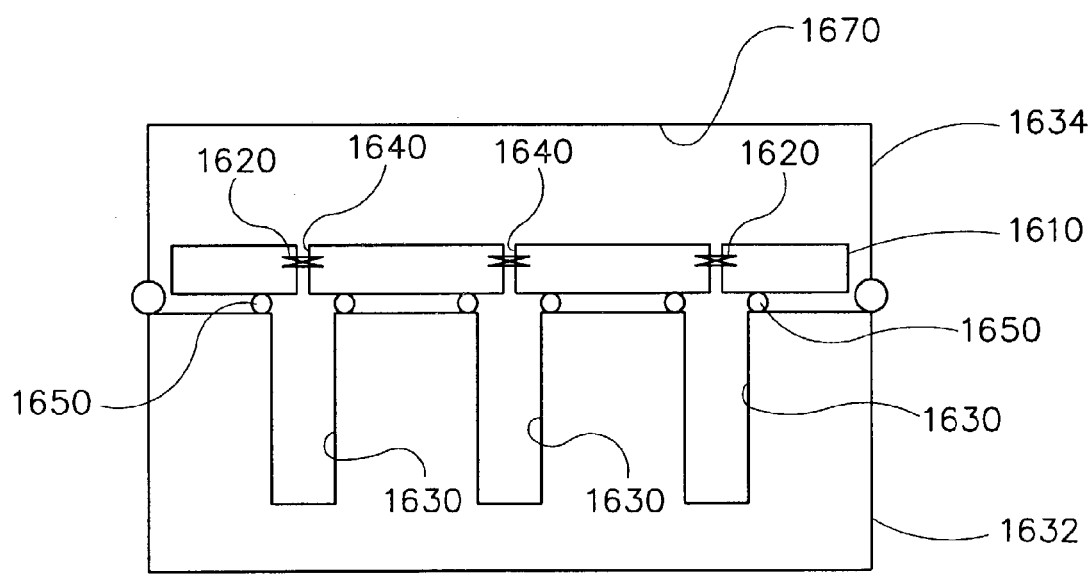
FIG. 16 is a schematic illustrating an array of microvalves contained within a substrate separate from the base of a reactor vessel.

FIG. 16 is a schematic of an alternative embodiment of the apparatus shown in FIG. 15. The apparatus includes a base 1632, cover 1634 configured to mate with the base and form a common pressure chamber 1670, reaction wells 1630 formed in the base, and a flow restriction device 1610. The flow restriction device 1610 includes a plurality of microvalves 1620 formed in a common substrate. The device 1610 is positioned on the base 1632 such that the microvalves 1620 align with reaction wells 1630 to restrict flow between reaction wells and common pressure chamber 1670. A sealing device, such as o-rings 1650 are preferably located at each reaction well 1630 and flow device 1610 interface. It is to be understood that the microvalves 1520, 1620 may be any type of flow restriction device including a check valve.

Figure 17:
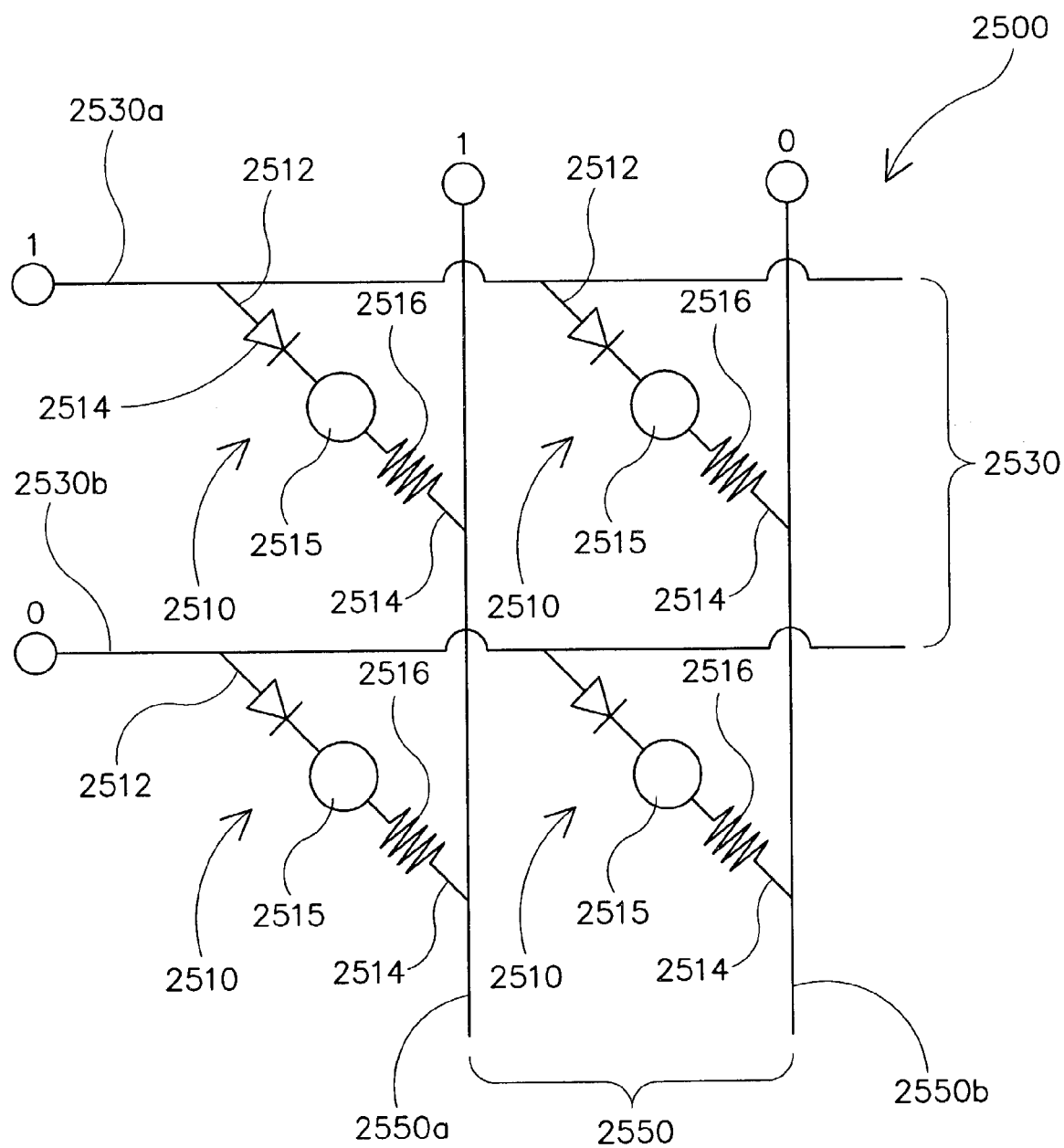
FIG. 17 is a schematic illustrating an array of microvalves and corresponding actuation system.
Figure 18:
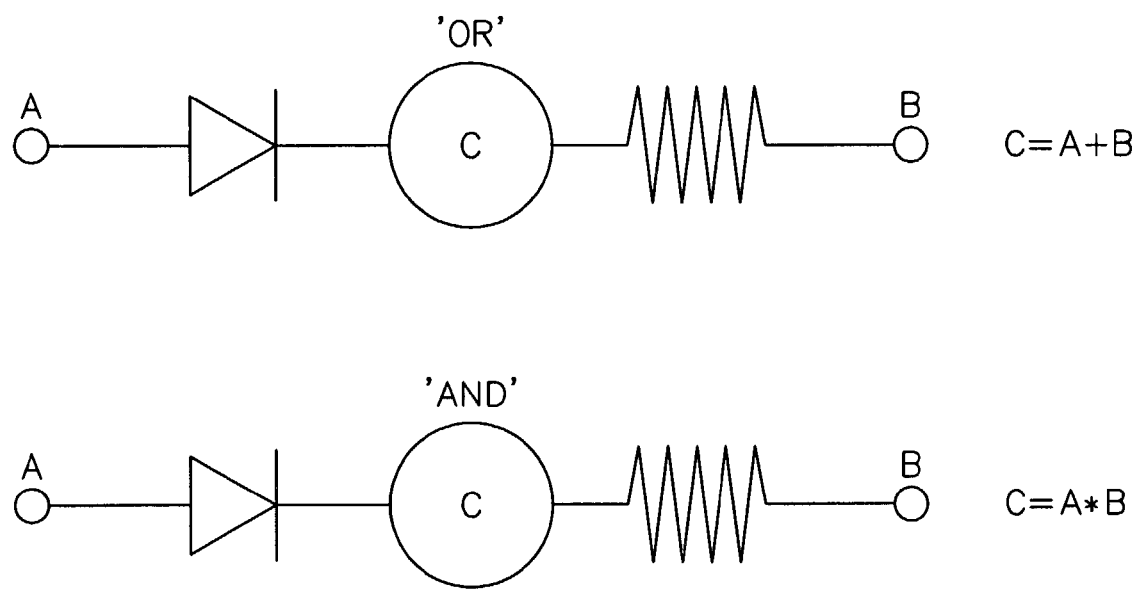
FIG. 18 is a schematic showing valve logic associated with the microvalves of FIG. 17.

In one embodiment, the microvalves shown schematically in FIGS. 15 and 16 may comprise an array of valves such as shown in FIG. 17. For example, pneumatically active microvalve array 2500 can comprise a plurality, and preferably four or more microvalves (2510—not shown schematically) in operational communication with four or more microvalve actuators 2515 arranged and/or formed at, on or in a common substrate. The microvalve actuators can actuate the microvalves. In some embodiments, the common substrate can comprise a plurality of laminae, and the four or more microvalves and four or more microvalve actuators 2515 can be formed in the plurality of laminae. Each of the four or more microvalve actuators 2515 can be in selective fluid communication between a first pneumatic valve actuating line 2530a, 2530b of a first set 2530 of actuating lines, and a second pneumatic valve actuating line sample line 2550a, 2550b of a second set 2550 of actuating lines. Collectively, the four or more microvalve actuators are in selective fluid communication between the sets of first and second valve actuating lines 2530 and lines 2550. As shown, each of the four or more actuating flowpaths comprises an actuator inlet 2512 in fluid communication with at least one of the first actuating lines 2530a, 2530b, and an actuator outlet 2514 in fluid communication with at least one of the second actuating lines 2550a, 2550b, and in selective fluid communication with the actuator inlet 2512. A valve control logic 2514 can provide for selective, controlled actuation of the microvalve actuator 2515 for operation of valve 2510. One or more flow restrictors 2516 can be provided in the actuator flowpath (i.e., between the actuator inlet 2512 and actuator outlet 2514), including for example as shown, between the microvalve actuator 2515 and the actuator outlet 2414. With reference to FIG. 18, the valve control logic 2514 can vary depending on the particular application, but can typically be an "AND" or an "OR" logic, such that valve control for four or more valves can be controlled using microprocessor based technology with appropriate software.

Although shown only with four or more microvalve actuators in the array, the number of microvalve actuators and microvalves can be substantially larger, including numbers that are the same as the number of reactors as described, for example, in Guan et al. (U.S. Pat. No. 6,149,882) and/or Bergh et al. (U.S. patent application Ser. No. 09/518,794), which are incorporated herein by reference in their entirety. As applied to chemical processing systems having arrays of larger numbers of components (e.g., reactors; microvalve actuators)—such as 100 or more components, the number of actuation circuits can be increased by log N (where N is the number of components) rather than being increased by N—which is the case with a hierarchy of individually-dedicated actuators. The array of microvalve actuators and microvalves can be fabricated by methods known in the art. See, for example: Rich et al., "*An 8-Bit Microflow Controller Using Pneumatically-Actuated Valves*", pp. 130–134, IEEE (1999); Wang et al., "*A Parylene Micro Check Valve*", pp. 177–182, IEEE (1999); Xdeblick et al., "*Thermpneumatically Actuated Microvalves and Integrated Electro-Fluidic Circuits*", 251–255, TRF, Solid State Sensor and Actuator Workshop, Hilton Head, S.C., Jun. 13–16 (1994); and Grosjean et al., "*A Practical Thermpneumatic Valve*", 147–152, IEEE (1999). In operation, the array of microvalves and microvalve actuators can provide for selective fluid communication between a plurality and preferably four or more reaction walls and the common pressure chamber.

Another example of microvalves and of a microvalve array that may be adapted for use in the flow restriction device of FIGS. 15 or 16 is described in U.S. patent application Ser. No. 10/092,035, entitled "Injection Valve Array", filed Mar. 6, 2002 by Bergh et al., (published as U.S. patent application Ser. No. 20020124897), which is incorporated by reference herein in its entirety.

Referring again to FIG. 14, a coil spring (or elastomeric material) may be placed at the bottom of each of the reaction wells to force the vials 190 upward and bias the open ends of the vials against the flow restriction device 192. The flow restriction device 192 is preferably removably attached to the base member with bolts 198 or other suitable attachment means. The flow restriction device 192 may also be coupled or integrally formed with the cover 134 so that the device is automatically disposed adjacent to the open ends of the reaction wells 130 when the cover is mated with the base member 132 and closed.

The materials of the base member 132, cover 134, flow restriction device 192, gasket 160, and vials 190 are preferably selected to be chemically suitable for the application (i.e., will not be attacked, solubilized, softened, or otherwise interact with the reagents, solvents, solids, products, or other components which are either added to the vessel or produced during a reaction sequence). The materials are also preferably chosen to assure that reactant, products, or by-products of the reaction are not adsorbed or otherwise trapped by the materials.

Although the present invention has been described in accordance with the embodiments shown, one of ordinary skill in the art will readily recognize that there could be variations made to the embodiments without departing from the scope of the present invention. By way of example, the configuration of gasket 92 may vary. Although gasket 92 has been shown as being substantially square in shape and including 64 openings 96, both the shape of gasket 92 and the number of openings 96 in gasket may vary. In one embodiment, gasket 92 may be extended to partially overlap a side section 710 (FIG. 7) of base 32 and, hence, incorporate some of the functionality served by o-ring 60. That is, gasket 92 may be configured to serve the functionality of both gasket 92 and o-ring 60.

In lieu of being formed as a single piece, gasket 92 may be formed from a plurality of different pieces. That is, gasket 92 may be formed as one or more smaller gaskets which, together, serve the functionality of gasket 92 and serve to seal wells 30 or vials 90 individually or in distinct groups.

Base 32 may be formed from any number of components. By way of example, wells 30 may be machined into base 32 such that base 32 is effectively formed from a single piece. Alternatively, base 32 may include a substantially separate substrate which includes wells 30. When base 32 includes a substantially separate substrate which includes wells 30, whenever it is desirable to chance the size of wells 30, or the configuration of wells 30, a different substrate may be inserted into base 32.

While the use of fasteners 54 has been described as being suitable for securing cover 35 to base 32, it should be understood that substantially any suitable method may be used to secure cover 35 to base 32. By way of example, cover 35 and base 32 may be threaded such that cover 35 may effectively be screwed into, or threaded directly to, base 32. Accordingly, it is intended that all matter contained in the above description and shown in the accompanying drawings shall be interpreted as illustrative and not in a limiting sense.

What is claimed is:

1. A parallel batch reactor for effecting chemical reactions, the parallel batch reactor comprising:
   a pressure chamber;
   an inlet port in fluid communication with the pressure chamber for pressurizing the pressure chamber from an external pressure source; and
   two or more reaction vessels within the pressure chamber, each of the two or more reaction vessels being in isolatable fluid communication with the pressure chamber such that during a first pressurizing stage of operation, each of the two or more reaction vessels can be simultaneously pressurized through common fluid communication with the pressure chamber, and such that during at least a second reaction stage of operation, each of the two or more pressurized reaction vessels can be fluidically isolated from each other.

2. The parallel batch reactor of claim 1 wherein the pressure chamber comprises a pressure chamber cover and a pressure chamber base, and the two or more reaction vessels are an array of reaction vessels formed in or supported by a common substrate, the reaction vessel base being adapted for receiving the array of reaction vessels.

3. The parallel batch reactor of claim 2 further comprising an array of microvalves configured to fluidically isolate said two or more reaction vessels from one another.

4. The parallel batch reactor of claim 3 wherein the array of microvalves is integrally formed with the base.

5. The parallel batch reactor of claim 3 wherein the array of microvalves is formed in a substrate independent from the base.

6. The parallel batch reactor of claim 1 wherein an isolated volume comprising each of the two or more reaction vessels is different than a volume of each of the two or more reaction vessels during said first pressurizing stage.

7. The parallel batch reactor of claim 1 wherein the two or more reaction vessels have different volumes during the second reaction stage of operation than in the first pressurizing stage of operation.

8. The parallel batch reactor of claim 1 wherein the two or more reaction vessels are fluidically isolated from each other by a check valve.

9. The parallel batch reactor of claim 1 wherein the two or more reaction vessels are fluidically isolated from each other by controlled microvalves.

10. The parallel batch reactor of claim 9 wherein the microvalves are integrally formed within a base of the reactor.

11. The parallel batch reactor of claim 9 wherein the microvalves are formed in a common substrate independent from a base of the reactor.

12. The parallel batch reactor of claim 1 wherein the two or more reaction vessels are fluidically isolated from each other by an isolation valve.

13. The parallel batch reactor of claim 1 wherein the two or more reaction vessels are fluidically isolated from each other by actuated valves.

14. The parallel batch reactor of claim 13 wherein the actuated valves are integrally formed within a base of the reactor.

15. The parallel batch reactor of claim 13 wherein the actuated valves are formed in a common substrate independent from a base of the reactor.

16. The parallel batch reactor of claim 1 wherein the two or more reaction vessels are fluidically isolated from each other by a flow restriction device.

17. The parallel batch reactor of claim 1 wherein the pressure chamber comprises a pressure chamber cover and a pressure chamber base, the batch reactor further comprising a reaction vessel cover being positionable to isolate each of the two or more pressurized reaction vessels during the second reaction stage of operation.

* * * * *